(12) United States Patent
Lewis et al.

(10) Patent No.: US 10,413,424 B2
(45) Date of Patent: Sep. 17, 2019

(54) INTERVERTEBRAL SPACERS AND RELATED METHODS AND INSTRUMENTS

(71) Applicant: CTL Medical Corporation, Addison, TX (US)

(72) Inventors: Chad Wayne Lewis, Layton, UT (US); Nathan Nelson, South Jordan, UT (US)

(73) Assignee: CTL Medical Corporation, Addison, TX (US)

( * ) Notice: Subject to any disclaimer, the term of this patent is extended or adjusted under 35 U.S.C. 154(b) by 0 days.

(21) Appl. No.: 16/002,714

(22) Filed: Jun. 7, 2018

(65) Prior Publication Data

US 2018/0280154 A1 Oct. 4, 2018

Related U.S. Application Data

(63) Continuation of application No. 14/801,665, filed on Jul. 16, 2015, now Pat. No. 9,993,352.

(60) Provisional application No. 62/025,444, filed on Jul. 16, 2014.

(51) Int. Cl.
| | |
|---|---|
| *A61F 2/44* | (2006.01) |
| *A61F 2/46* | (2006.01) |
| *A61B 17/80* | (2006.01) |
| *A61B 17/16* | (2006.01) |
| *A61B 17/88* | (2006.01) |
| *A61F 2/30* | (2006.01) |

(52) U.S. Cl.
CPC .......... *A61F 2/447* (2013.01); *A61B 17/1631* (2013.01); *A61B 17/1633* (2013.01); *A61B 17/8033* (2013.01); *A61B 17/8875* (2013.01); *A61F 2/4455* (2013.01); *A61F 2/4611* (2013.01); *A61F 2002/305* (2013.01); *A61F 2002/30014* (2013.01); *A61F 2002/30433* (2013.01); *A61F 2002/30492* (2013.01); *A61F 2002/30782* (2013.01); *A61F 2002/30904* (2013.01); *A61F 2002/448* (2013.01); *A61F 2002/4623* (2013.01)

(58) Field of Classification Search
CPC .............. A61F 2/442; A61F 2002/4435; A61F 2002/4445; A61F 2002/445
USPC .................. 606/246, 248, 249, 288–291; 623/17.11–17.16
See application file for complete search history.

(56) References Cited

U.S. PATENT DOCUMENTS

| | | | | |
|---|---|---|---|---|
| 2012/0053638 A1* | 3/2012 | Rusch | ................ | A61B 17/8047 606/287 |
| 2012/0271423 A1* | 10/2012 | Wallenstein | ....... | A61B 17/8685 623/17.16 |
| 2013/0166032 A1* | 6/2013 | McDonough | ......... | A61F 2/4455 623/17.16 |

* cited by examiner

*Primary Examiner* — Julianna N Harvey
*Assistant Examiner* — Christina Negrellirodriguez
(74) *Attorney, Agent, or Firm* — Carrington, Coleman, Sloman & Blumenthal, L.L.P.

(57) ABSTRACT

Biomedical implants comprising portions made of disparate materials, such as intervertebral implants and related methods and instruments. In some embodiments, the implant may comprise a base portion comprising a first material and a secondary fastener portion comprising a second material having distinct physical properties relative to the first material. The secondary portion may wholly define a front end wall surface of the implant, and the base portion and the secondary portion may collectively define at least one of an upper surface and a lower surface of the implant.

18 Claims, 29 Drawing Sheets

INTERVERTEBRAL SPACERS AND RELATED METHODS AND INSTRUMENTS

RELATED APPLICATIONS

This application is a continuation application of U.S. patent application Ser. No. 14/801,665 filed on Jul. 16, 2015, and titled "INTERVERTEBRAL SPACERS AND RELATED METHODS AND INSTRUMENTS" which claims the benefit of priority of U.S. Provisional Patent Application No. 62/025,444 filed Jul. 16, 2014 and titled "INTERVERTEBRAL SPACERS AND RELATED METHODS AND INSTRUMENTS". Both of the aforementioned applications are incorporated by reference herein in their entireties.

SUMMARY

Various embodiments of apparatus, methods, and systems are disclosed herein that relate to biomedical implants and instruments for installing such implants. In preferred embodiments and implementations, the biomedical implants comprise spinal implants. For example, some embodiments may comprise stand-alone anterior lumbar interbody (ALIF) fusion implants. Some embodiments may comprise instruments for installing such intervertebral spinal implants, including inserters, instrument guide tubes, instrument guide tube handles, flexible instruments and instrument tips, and screw driver tips. However, it should be understood that many of the concepts disclosed herein may be applied to other intervertebral spinal implants, including those designed for ALIF fusion with pedicle screws or other fixation mechanisms, for posterior lumbar interbody fusion (PLIF), for transforaminal lumbar interbody fusion (TLIF), for direct lateral interbody fusion (DLIF), and the like. Moreover, still other principles, components, elements, and/or features disclosed herein may be applicable to other biomedical implants.

In some preferred embodiments, different types of materials may be combined in a single implant. For example, a relatively non-threadable materials and/or a material capable of having relatively less strong/stabile threads may be used for a base portion of an implant and one or more plates, sleeves, inserts, or other secondary portion(s) of an implant may comprise a more readily threadable material and/or a material capable of having relatively more strong/stabile threads. Such configurations may be useful in that they allow for use of a more easily threadable material for receipt of bone screws, or a material that will more readily receive/accept screws, along with another material with other, more desirable characteristics for serving as the primary or base portion of an intervertebral implant.

In a more particular example of an intervertebral spinal implant, such as in some embodiments a standalone anterior lumbar interbody fusion implant, according to some embodiments, the implant may comprise a base portion comprising a first material and a secondary portion comprising a second material, wherein the second material is distinct from the first material. The second material preferably has distinct physical properties relative to the first material. In some embodiments, the secondary portion may wholly define a front end wall surface of the intervertebral spinal implant, and the base portion and the secondary portion may collectively define at least one of an upper surface and a lower surface of the intervertebral spinal implant. In some embodiments, the base portion and the secondary portion may collectively define both the upper surface and the lower surface of the implant.

Some embodiments may further comprise a locking member for coupling the base portion to the secondary portion. Some such embodiments may further comprise a second locking member for coupling the base portion to the secondary portion. In some such embodiments, the base portion may at least partially (in some embodiments, fully) define a first sidewall of the spinal implant and at least partially (in some embodiments, fully) define a second sidewall of the spinal implant opposite from the first sidewall. Thus, the locking member may be configured to couple the secondary portion to the base portion at the first sidewall, and at the second sidewall.

In some embodiments, the secondary portion may comprise at least one threaded bone screw opening configured to receive a bone screw therethrough.

In another example of an intervertebral spinal implant, according to certain preferred embodiments, the implant may comprise a base portion comprising a first material. The base portion may comprise an opening. The implant may further comprise a secondary fastener portion comprising a second material, wherein the second material is distinct from the first material, and wherein the second material has distinct physical properties relative to the first material. The secondary fastener portion may be configured to be received in the opening, and may further be configured to engage with a fastener such that the secondary fastener portion is positioned in between the fastener and the base portion. Some embodiments may comprise a plurality of secondary fastener portions configured to be received in a plurality of openings formed within the base portion.

In some embodiments, the fastener or fasteners may comprise a bone screw configured to extend through the intervertebral spinal implant and engage a vertebral body of a patient's spine.

In some embodiments, the secondary fastener portion(s) may be configured to prevent contact between the fastener and the base portion.

In some embodiments, the secondary fastener portion(s) may comprise an internal thread. In some such embodiments, the internal thread may extend about an internal periphery of the secondary fastener portion(s) between about one turn and about two turns. In some such embodiments, the internal thread may extend about this internal periphery by about one turn.

In some embodiments, the secondary fastener portion may comprise an engagement feature configured to engage with a corresponding engagement feature of the base portion. In some such embodiments, the engagement feature of the fastener portion may comprise a protruding rim, and the engagement feature of the base portion may comprise a slot formed within the opening, or vice versa.

In some embodiments, the secondary fastener portion may comprise means for preventing the secondary fastener portion from rotating with respect to the base portion, such as a protrusion formed on the secondary fastener portion configured to be received in a groove formed within the base portion, or vice versa.

In another example of a spinal implant according to certain embodiments, the implant may comprise a base portion comprising a first material. The base portion may at least partially define a first sidewall of the spinal implant, and may further at least partially define a second sidewall of the spinal implant opposite from the first sidewall. The base portion may wholly define a first end wall of the spinal implant, and the base portion may lack an end wall opposite from the first end wall. The implant may further comprise a secondary portion comprising a second material that is distinct from the first material and has distinct physical properties relative to the first material. The secondary portion may be coupled to the base portion at the first sidewall and at the second sidewall such that the secondary portion at least partially defines a second end wall of the spinal implant opposite from the first end wall. In some embodiments, the secondary portion may wholly define the second end wall.

In some embodiments, the secondary portion may bridge a gap between a first end of the first sidewall and a first end of the second sidewall of the base portion so as to wholly define the second end wall. In some such embodiments, the base portion may at least substantially comprise a "C" shape.

The features, structures, steps, or characteristics disclosed herein in connection with one embodiment may be combined in any suitable manner in one or more alternative embodiments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
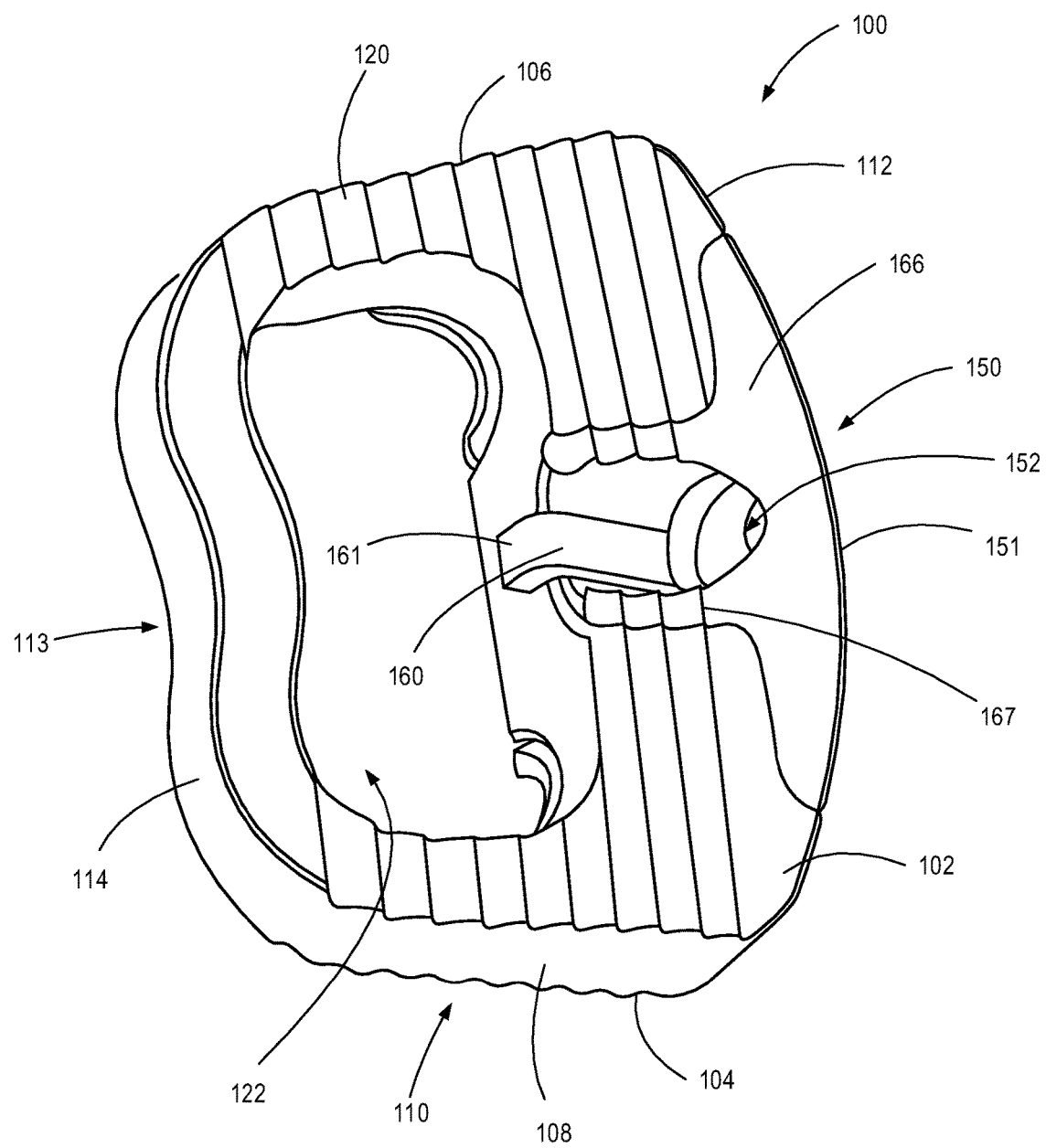
FIG. 1 is a perspective view of an embodiment of a stand-alone anterior lumbar interbody fusion spinal implant.

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

Various embodiments of apparatus, methods, and systems are disclosed herein that relate to intervertebral spinal implants and instruments for installing such implants. For example, some embodiments may comprise stand-alone anterior lumbar interbody (ALIF) fusion implants. Some embodiments may comprise instruments for installing such intervertebral spinal implants, including inserters, instrument guide tubes, instrument guide tube handles, flexible instruments and instrument tips, and screw driver tips. However, it should be understood that many of the concepts disclosed herein may be applied to other intervertebral spinal implants, including those designed for ALIF fusion with pedicle screws or other fixation mechanisms, for posterior lumbar interbody fusion (PLIF), for transforaminal lumbar interbody fusion (TLIF), for direct lateral interbody fusion (DLIF), and the like.

In some embodiments, different types of materials may be combined in a single implant. For example, a ceramic material, such as a silicon nitride ceramic material, may be used for a base portion of an implant and one or more plates, sleeves, inserts, or other secondary portion(s) of an implant may comprise another material or materials, such as titanium another metal, or a plastic, such as PEEK, for example. Such configurations may be useful in that they allow for use of a more easily threadable material for receipt of bone screws, or a material that will more readily receive/accept screws, along with another material with other, more desirable characteristics for serving as the primary or base portion of an intervertebral implant, such as silicon nitride ceramic, another ceramic, or another material having distinct properties relative to the other portion of the device.

Examples of suitable silicon nitride materials are described in, for example, U.S. Pat. No. 6,881,229, titled "Metal-Ceramic Composite Articulation," which is incorporated by reference herein. In some embodiments, dopants such as alumina ($Al_2O_3$), yttria ($Y_2O_3$), magnesium oxide, and strontium oxide, can be processed to form a doped composition of silicon nitride. In some embodiments, powders of silicon nitride may be used to form the ceramic implants, either alone or in combination with one or more of the dopants referenced above. Other examples of suitable silicon nitride materials are described in U.S. Pat. No. 7,666,229 titled "Ceramic-Ceramic Articulation Surface Implants," which is hereby incorporated by reference. Still other examples of suitable Silicon Nitride materials are described in U.S. Pat. No. 7,695,521 titled "Hip Prosthesis with Monoblock Ceramic Acetabular Cup," which is also hereby incorporated by reference.

Additional details regarding certain preferred embodiments will now be described in greater detail with reference to the accompanying drawings. FIG. 1 depicts a perspective view of an embodiment of a standalone ALIF implant 100. Implant 100 comprises a base portion 110 and a secondary portion 150. Base portion 110 and secondary portion 150 preferably comprise different materials such that implant 100 may take advantage of the different characteristics of the two different materials in the same implant. For example, in some embodiments, base portion 110 may comprise a silicon nitride ceramic material or another similar ceramic material. Secondary portion 150 may comprise a metal, such as a titanium metal or titanium alloy.

Base portion 110 of implant 100 comprises an upper surface 102, a lower surface 104, a first side wall surface 106, a second side wall surface 108 opposite from surface 106, a front end wall surface 112, and a rear end wall surface 114 opposite from front end wall surface 112. Front end wall surface 112 comprises a recess configured to facilitate coupling with secondary portion 150.

Upper and lower surfaces 102 and 104 may both comprise a plurality of engagement structures 120, which, in the depicted embodiment, comprise rows of teeth. Teeth 120 may be arranged in parallel rows that may each extend at least substantially perpendicular to the direction in which side wall surfaces 106 and 108 extend.

Upper surface 102 also comprises an opening 122. Opening 122 also extends through lower surface 104 to allow for ingrowth of bony material therethrough. As those of ordinary skill in the art will appreciate, other embodiments are contemplated in which multiple such openings extend between upper surface 102 and lower surface 104.

Figure 2:
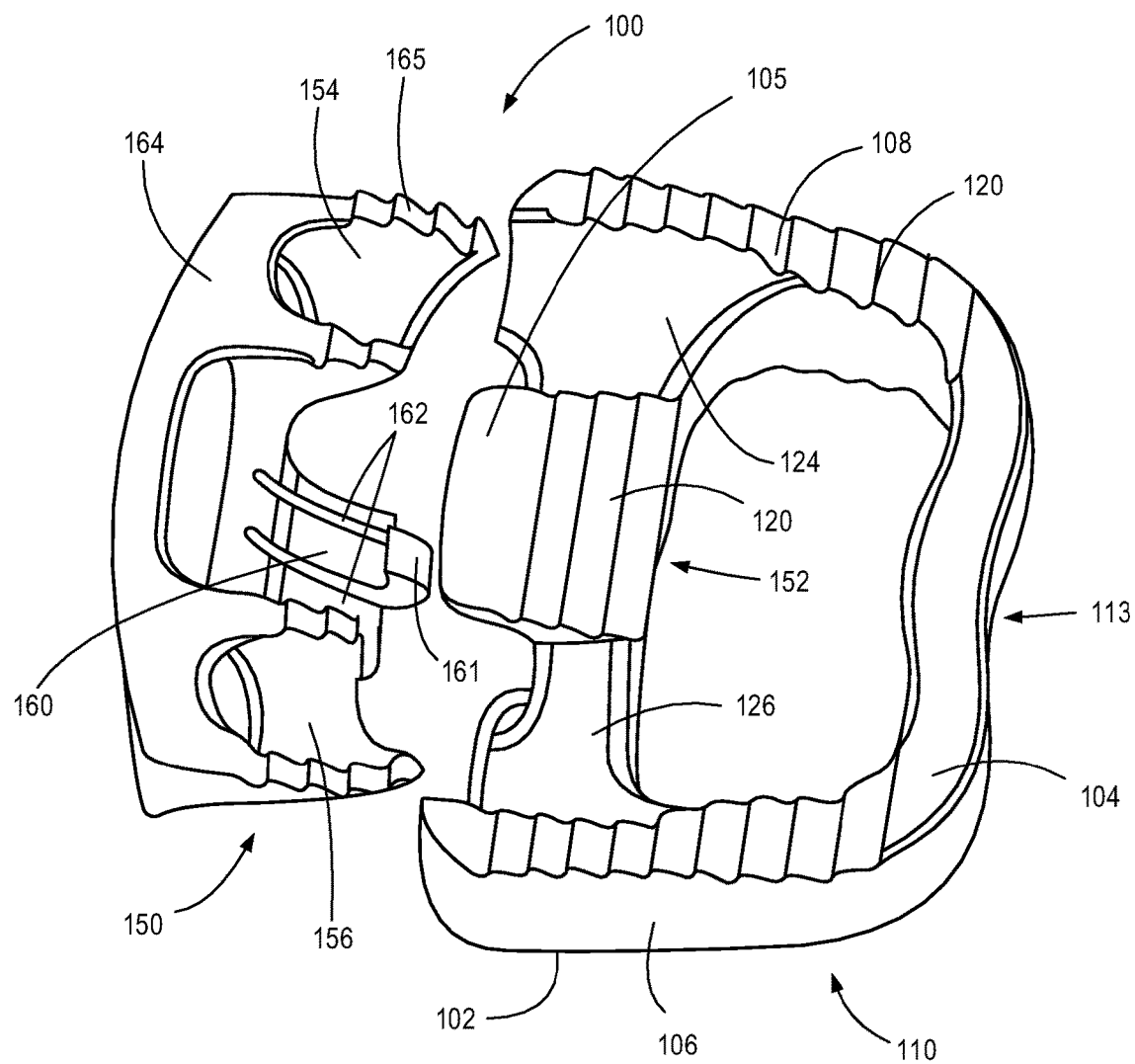
FIG. 2 is an exploded perspective view of the spinal implant of FIG. 1.

In the depicted embodiment of FIGS. 1 and 2, secondary portion 150 comprises an insert configured to receive fasteners, such as bone screws, therethrough. Other types of fasteners that may be usable with one or more of the embodiments disclosed herein may include dowels, pins, nails, pegs, and expandable screws/pegs/pins, etc. Thus, secondary portion 150 may be considered a secondary fastener portion or an insert. Insert 150 comprises three fastener openings, namely, fastener openings 152, 154, and 156. Each of these fastener openings may be configured to receive a bone screw (not shown) or another such fastener. Fastener openings 152, 154, and 156 may be threaded in some embodiments.

Fastener opening 152 extends from a surface 151 of secondary portion 150 that is configured to smoothly transition with front end wall surface 112 of base portion 110. Thus, implant 100 comprises a front end wall surface defined in part by front end wall surface 112 of base portion 110 and surface 151 of secondary portion 150. As best seen in FIG. 1, fastener opening 152 is configured to direct a screw or other fastener through upper surface 102. In alternative embodiments, however, one or more surfaces of implant 100 may be fully-defined by secondary portion 150. Thus, in alternative embodiments, front end wall surface 112 may be fully defined by surface 151 of secondary portion 150.

As also depicted in FIG. 1, secondary portion 150 further comprises a tab 160. Tab 160 is configured to engage base portion 110 to secure secondary portion 150 to base portion 110. In alternative embodiments, however, one or more such tabs may instead be formed on base portion 110 and be configured to engage a structure or other part of secondary portion 150. In the depicted embodiment, tab 160 is configured to extend over and engage a part of base portion 110 that defines opening 122. In some embodiments, multiple tabs may be used to facilitate such securement.

As shown in FIGS. 1 and 2, tab 160 may comprise a hook-shaped end 161 to further facilitate engagement with base portion 110. In addition, in some embodiments, a corresponding recess, depression, and/or mating feature may be formed on base portion 110 to provide for a more secure engagement. Tab 160 may also be flexible to allow it to flex away from and then resiliently flex towards base portion 110. Tab 160 may also be formed from the surface/material defining fastener opening 152.

More particularly, in the depicted embodiment, as best seen in the exploded view of FIG. 2, tab 160 is at least partially defined by two parallel slits 162 formed within the material defining fastener opening 152. This may allow tab 160 to flex into and away from fastener opening 152, which may allow for hook-shaped portion 161 to flex away from and resiliently engage base portion 110. Because another portion of secondary portion 150 engages an opposite surface of base portion 110, as described in greater detail below, a single tab 160 may provide sufficient force to keep these two pieces securely engaged to one another. However, as previously mentioned, other embodiments are contemplated in which multiple tabs may be used.

Fastener openings 154 and 156 are best seen in FIG. 2. As seen in this figure, fastener openings 154 and 156 are partial holes. In other words, fastener openings 154 and 156 comprise in cross section only partial, unclosed circles, ovals, or the like. However, these openings may be sufficiently near fully closed in order to hold screws or other fasteners in place. Still, it should be understood that other embodiments are contemplated in which these fasteners comprise fully-closed holes.

Fastener openings 154 and 156 may be configured to engage recesses 124 and 126, respectively, formed within base portion 110. Thus, after tab 160 has been engaged with base portion 110, as shown in FIG. 1, tab 160 may be configured to resiliently bias recesses 124 and 126 against portions of secondary portion 150 that define fastener openings 154 and 156.

As also depicted in FIG. 2, secondary portion 150 may comprise a lower surface 164 comprising teeth 165 positioned on opposite sides of fastener openings 154 and 156. Teeth 165 may be configured to be aligned with teeth 120 when secondary portion 150 has been engaged with base portion 110. Similarly, secondary portion 150 may comprise an upper surface 166 comprising teeth 167 positioned on opposite sides of fastener opening 152, as shown in FIG. 1. As also shown in FIG. 1, teeth 167 may be configured to align with teeth 120 of base portion 110 when base portion 110 has been engaged with secondary portion 150.

As depicted in FIG. 2, teeth 120 on upper surface 102 may be partially positioned on an island 105 positioned in between the two side wall surfaces 106 and 108. The teeth on island 105 may be configured to match and align with corresponding teeth 165 positioned interiorly with respect to and adjacent to fastener openings 154 and 156.

Rear end wall surface 114 may comprise a centrally-located concavity 113, as depicted in FIGS. 1 and 2. Concavity 113 may be configured to accommodate a patient's spinal cord or otherwise conform to certain anatomical features of a spinal column.

Figure 3:
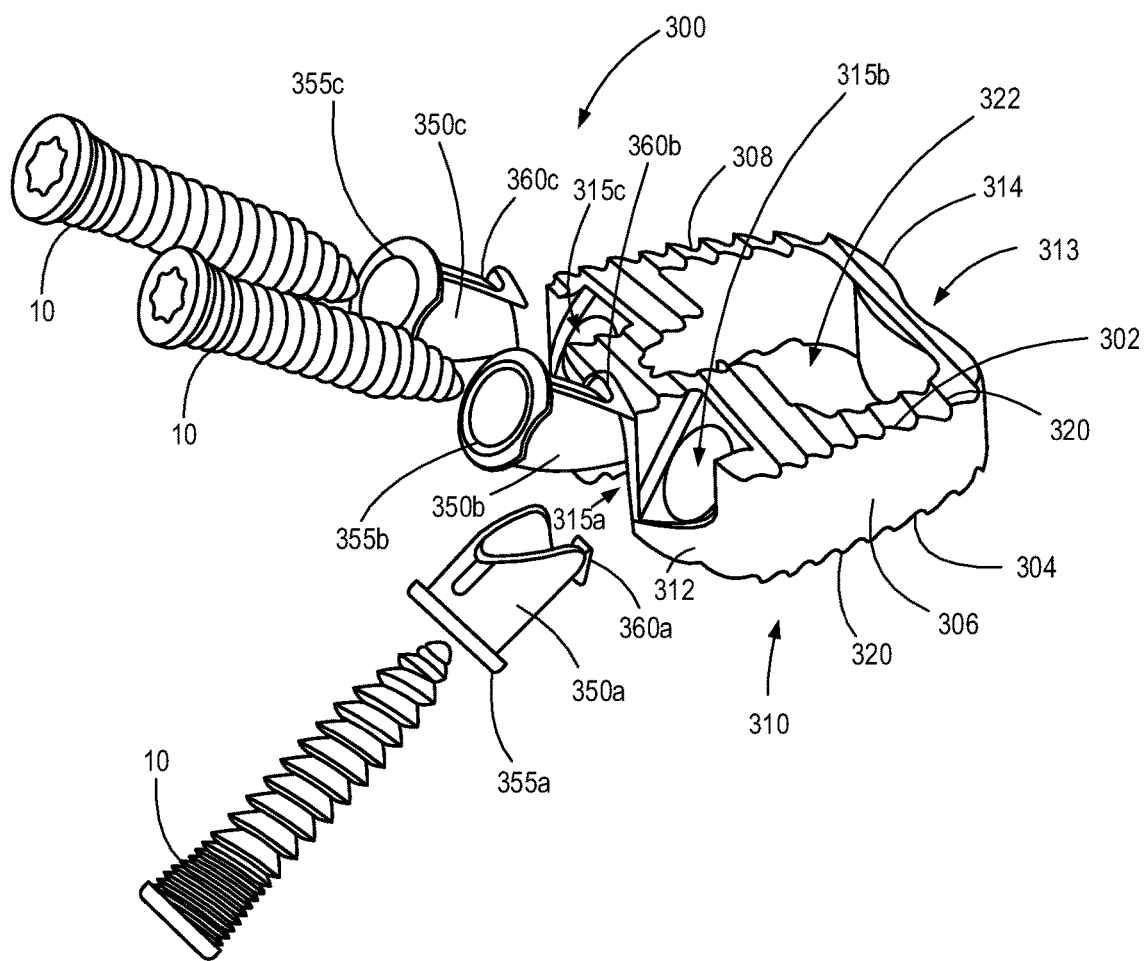
FIG. 3 is an exploded perspective view of another embodiment of a stand-alone anterior lumbar interbody fusion spinal implant.
Figure 4:
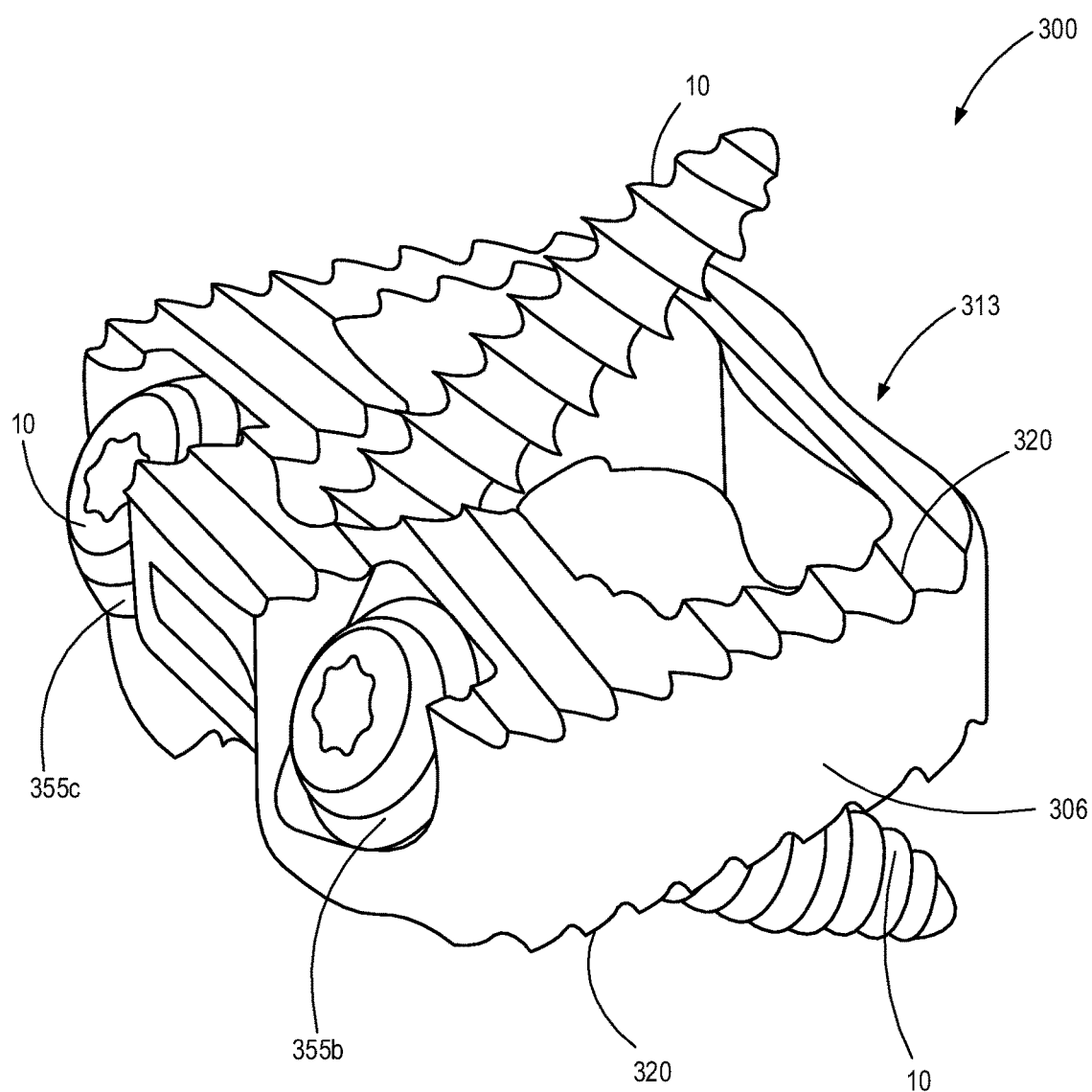
FIG. 4 is a perspective view of the spinal implant of FIG. 3.

FIGS. 3 and 4 depict an alternative embodiment of a stand-alone ALIF implant 300. Implant 300 comprises a base portion 310 and a plurality of secondary fastener portions 350a-c. Base portion 310 and secondary fastener portions 350a, 350b, and 350c, respectively, preferably comprise different materials such that implant 300 may take advantage of the different characteristics of the two different materials in the same implant. For example, in some embodiments, base portion 310 may comprise a silicon nitride ceramic material or another similar ceramic material and secondary fastener portions 350a-c may each comprise a metal, such as a titanium metal or titanium alloy.

Base portion 310 comprises an upper surface 302, a lower surface 304, a first side wall surface 306, a second side wall surface 308 opposite from surface 306, a front end wall surface 312, and a rear end wall surface 314 opposite from front end wall surface 312. Front end wall surface 312 comprises three recesses 315a-c configured to facilitate coupling with secondary fastener portions 350a-c, respectively. Rear end wall surface 314 comprises a centrally-located concavity 313, which may be configured to accommodate a patient's spinal cord or otherwise conform to certain anatomical features of a spinal column.

In the embodiment of FIGS. 3 and 4, secondary fastener portions 350a-c each comprise sleeves configured to engage with a single screw or other fastener and facilitate coupling of such fastener/screw with base portion 310. More particularly, as shown in FIG. 3, bone screws 10 are configured to each fit within a corresponding sleeve 350. Two of the bone screws 10 are configured to extend through one of the two opposing surfaces for contacting vertebrae (in the depicted embodiment, lower surface 304), and one of the bone screws 10 is configured to extend through an opposite surface (in the depicted embodiment, upper surface 302). However, a wide variety of alternative embodiments are contemplated in which any desired number of fasteners extending through any of the various surfaces may be used.

Upper surface 302 comprises an opening 322 that extends through lower surface 304 to allow for ingrowth of bony material therethrough. Upper and lower surfaces 302 and 304 may both comprise a plurality of engagement structures 320, which, in the depicted embodiment, comprise rows of teeth. Teeth 320 may be arranged in parallel rows that may each extend at least substantially perpendicular to the direction in which side wall surfaces 306 and 308 extend.

In the embodiment of FIGS. 3 and 4, sleeves 350a-c are each configured to be received in a sleeve recess formed within base portion 310. In some embodiments, sleeves 350a-c may be threaded to facilitate desired coupling with respective bone screws 10 or other fasteners.

Each of sleeves 350a-c comprises a tab—tabs 360a-c, respectively—configured to facilitate fixed engagement between the sleeves and base portion 310. In the depicted embodiment, each of tabs 360a-c is configured to extend over and engage a part of base portion 310 that defines opening 322.

As shown in FIG. 3, tabs 360a-c may comprise hook-shaped ends to further facilitate engagement with base portion 310. In addition, in some embodiments, a corresponding recess, depression, and/or mating feature may be formed on base portion 310 to provide for a more secure engagement. Tabs 360a-c may also be flexible to allow them to flex away from and then resiliently flex towards base portion 310. Tabs 360a-c may also be formed from the same surface/material defining the holes formed in sleeves 350a-c.

More particularly, in the depicted embodiment, tabs 360a-c may, like tabs 160 of implant 100, be respectively defined by two parallel slits formed within sleeves 350a-c. This allows tabs 360a-c to flex into and away from sleeve recesses 315a-c, which may allow for hook-shaped portions formed on the ends of tabs 360a-c to flex away from and resiliently engage base portion 310.

Each of the various sleeves 350a-c may further comprise a corresponding rim 355a-c. These rims 355 may be sized so as to prevent the sleeves 350 from passing all the way through sleeve recesses 315a-c. In addition, the interior of sleeves 350a-c and/or the heads of screws 10 may be dimensioned so as to prevent the screws from passing through one or more portions of sleeves 350a-c.

Figure 5:
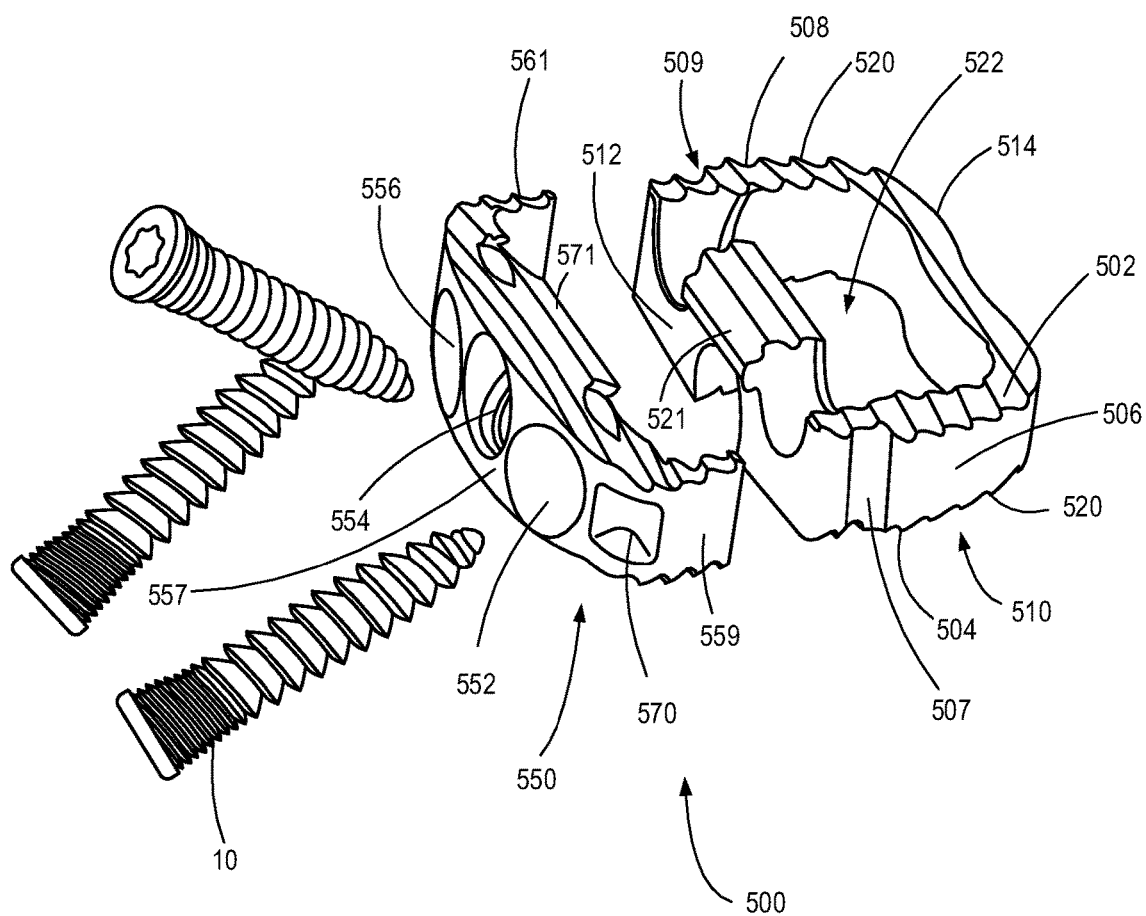
FIG. 5 is an exploded perspective view of still another embodiment of a stand-alone anterior lumbar interbody fusion spinal implant.

FIG. 5 depicts another embodiment of a stand-alone ALIF implant 500. Implant 500 comprises a base portion 510 and a secondary fastener portion 550. Again, base portion 510 and secondary portion 550 preferably comprise different materials such that implant 500 may take advantage of the different characteristics of the two different materials in the same implant. For example, in some embodiments, base portion 510 may comprise a silicon nitride ceramic material or another similar ceramic material, and secondary fastener portion 550 may comprise other materials more suitable for engaging a threaded fastener, such as titanium metals, titanium alloys, or other metals.

Base portion 510 of implant 500 comprises an upper surface 502, a lower surface 504, a first side wall surface 506, a second side wall surface 508 opposite from surface 506, a front end wall surface 512, and a rear end wall surface 514 opposite from front end wall surface 512.

Upper and lower surfaces 502 and 504 may both comprise a plurality of engagement structures or teeth 520. Teeth 520 may be arranged in parallel rows that may each extend at least substantially perpendicular to the direction in which side wall surfaces 506 and 508 extend. Upper surface 502 also comprises an opening 522 that also extends through lower surface 504 to allow for ingrowth of bony material therethrough.

In the embodiment of FIG. 5, secondary fastener portion 550 comprises a plate configured to fit over and engage with front end wall surface 512 and further configured to receive fasteners, such as bone screws, therethrough. Plate 550 comprises three fastener openings, namely, fastener openings 552, 554, and 556. Each of these fastener openings may be configured to receive a bone screw 10 or another such fastener. Fastener openings 552, 554, and 556 may be threaded in some embodiments.

Fastener openings 552, 554, and 556 extend from a front surface 557 of secondary portion 550 such that implant 500 comprises a front end wall surface defined in whole by front end wall surface 557 of secondary portion 550. Secondary portion 550 further comprises two opposing flanges 559 and 561 that may be configured to be received in corresponding depressions 507 and 509 formed in side wall surfaces 506 and 508 of base portion 510. In some embodiments, lips or hook structures may be formed at the end of flanges 559 and 561 to further facilitate a secure coupling between base portion 510 and secondary fastener portion 550.

As also shown in FIG. 5, a shelf 521 may be formed on base portion 510, which may further facilitate desired coupling between base portion 510 and secondary fastener portion 550. Shelf 521 may extend from the distal surface of front end wall surface 512, and may be configured to engage a corresponding structure, such as shelf 571, on secondary fastener portion 550. In some embodiments, shelves 521 and 571 may be configured to engage in a nesting fashion and may therefore have shapes suitable for such engagement. In some embodiments, additional shelves may be formed adjacent to lower surface 504 if desired. In still other embodiments, flanges 559 and 561 may not extend the entire distance between upper surface 502 and lower surface 504, and depressions 507/509 may similarly not extend this entire distance such that flanges 559 and 561 are prevented from moving up and/or down with respect to base portion 510 by virtue of a "roof" and a "floor" to depressions 507/509. This may be done as an alternative to, or in addition to, providing the shelves referenced above.

Implant 500 further comprises slots 570 formed within the front surface of secondary fastener portion 550. Although only one slot 570 is depicted in FIG. 5, it should be understood that another similar slot 570 may also be formed on the opposite side of secondary fastener portion 550. These slots 570 may be configured to be engaged with corresponding tabs, protrusions, or other engagement structures formed on an inserter or other instrument, which may be used to squeeze and/or grip implant 500.

Figure 6:
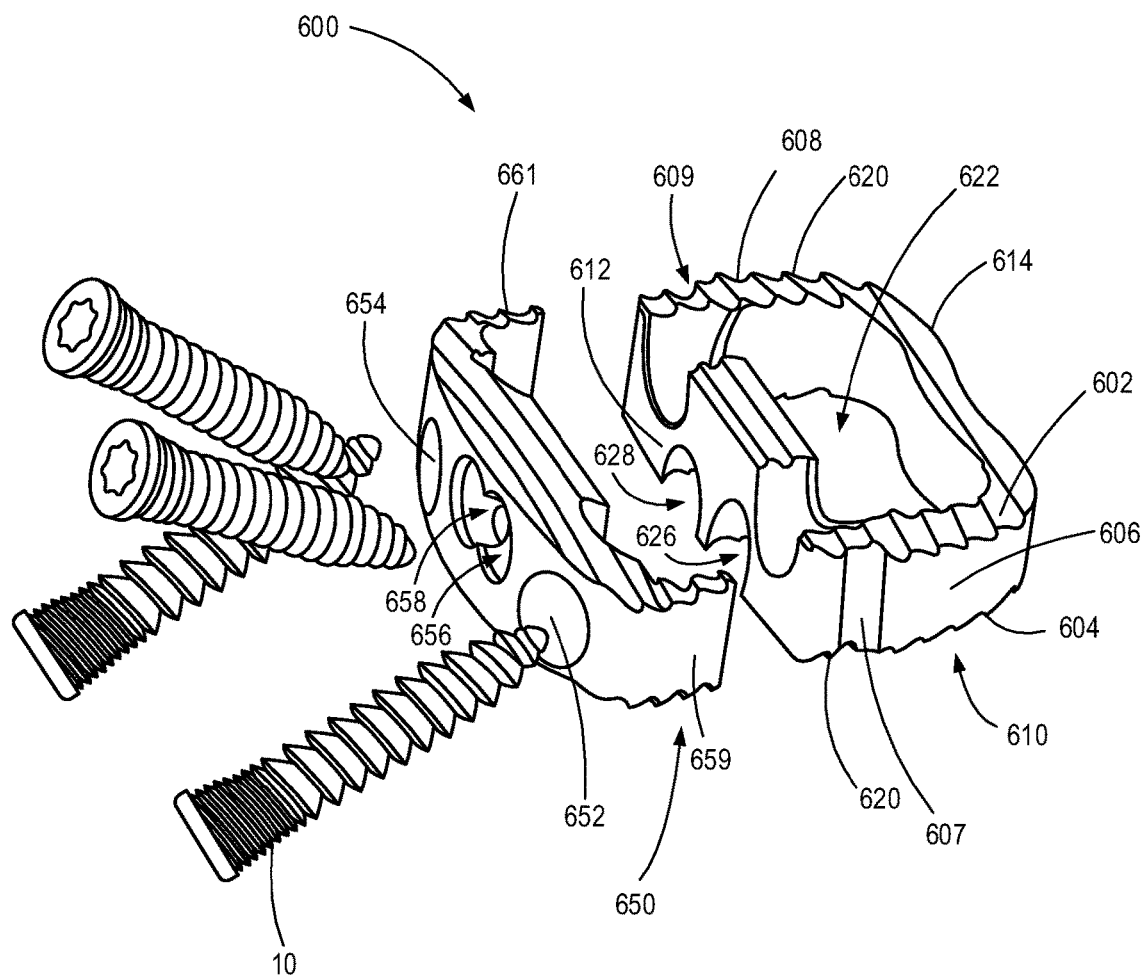
FIG. 6 is an exploded perspective view of yet another embodiment of a stand-alone anterior lumbar interbody fusion spinal implant.

FIG. 6 depicts still another embodiment of a stand-alone ALIF implant 600. Implant 600 is similar to implant 500 with a few exceptions. For example, implant 600 is configured to receive four bone screws 10, two of which are configured to extend through the upper surface 602 and two of which are configured to extend through the lower surface 604. In addition, although, like implant 500, implant 600 comprises a separate fastener opening for each fastener, namely, fastener openings 652, 654, 656, and 658. Two of these fastener openings overlap. In particular, fastener openings 656 and 658 overlap but extend through two separate partial fastener openings or recesses formed in base portion 610, namely, fastener openings 626 and 628, respectively. In other embodiments, fastener openings 626 and 628 may be combined into a single recess or opening configured to receive two or more separate fasteners.

In most other respects, implant 600 is similar to implant 500. Thus, implant 600 comprises a base portion 610 and a secondary fastener portion 650 comprising a plate. Base portion 610 comprises an upper surface 602, a lower surface 604, a first side wall surface 606, a second side wall surface 608 opposite from surface 606, a front end wall surface 612, and a rear end wall surface 614 opposite from front end wall surface 612.

Similarly, upper and lower surfaces 602 and 604 both comprise a plurality of engagement structures or teeth 620, which may be arranged in parallel rows that may each extend at least substantially perpendicular to the direction in which side wall surfaces 606 and 608 extend. Upper surface 602 also comprises an opening 622 that also extends through lower surface 604 to allow for ingrowth of bony material therethrough.

Secondary portion 650 further comprises two opposing flanges 659 and 661 that may be configured to be received in corresponding depressions 607 and 609 formed in side wall surfaces 606 and 608 of base portion 610. However, unlike implant 500, implant 600 lacks corresponding shelf structures to further facilitate coupling between base portion 610 and secondary portion 650. Given a sufficiently-tight engagement between flanges 659/661 and depressions 607/609, such features may be unnecessary for certain applications and embodiments.

Figure 7:
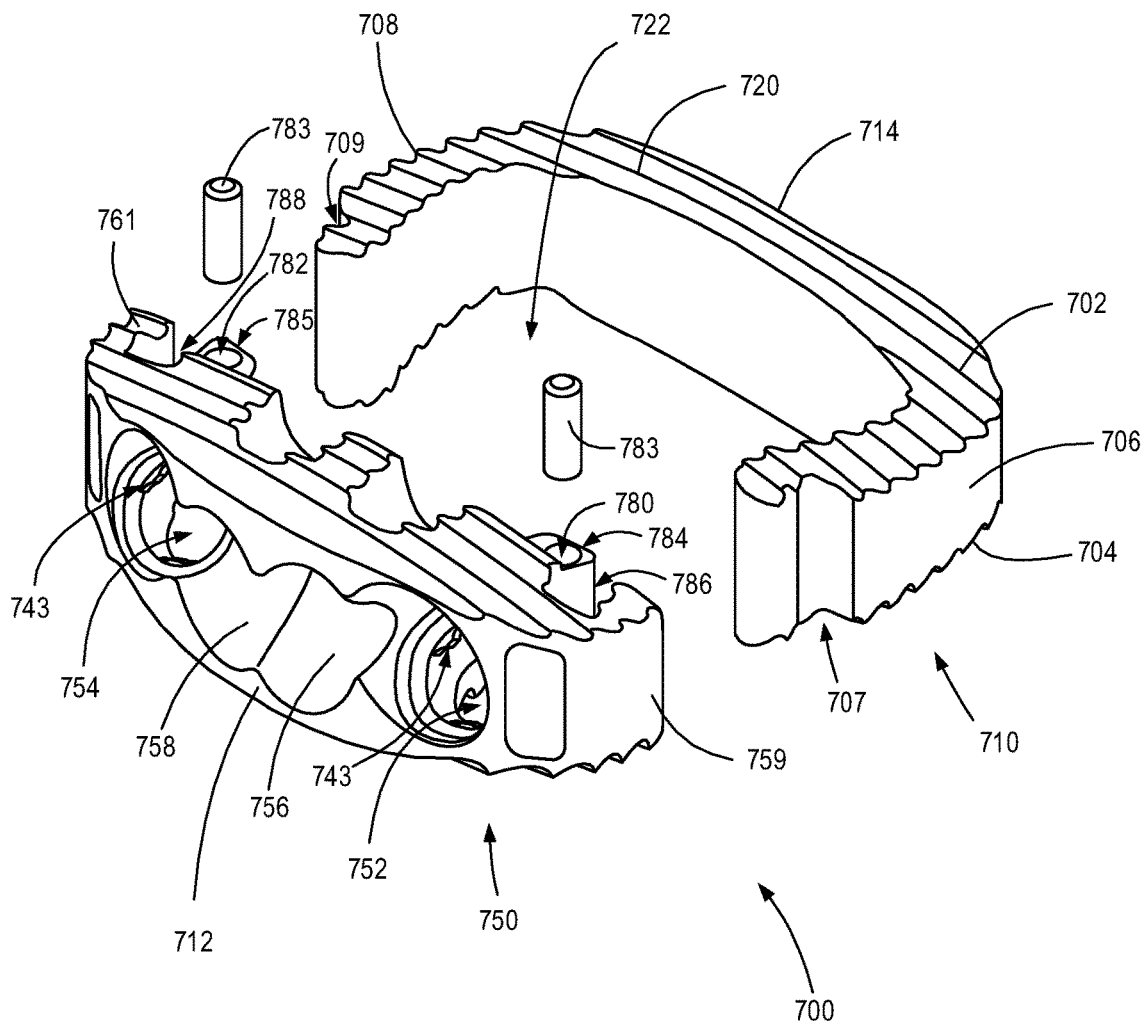
FIG. 7 is an exploded perspective view of still another embodiment of a stand-alone anterior lumbar interbody fusion spinal implant.
Figure 8:
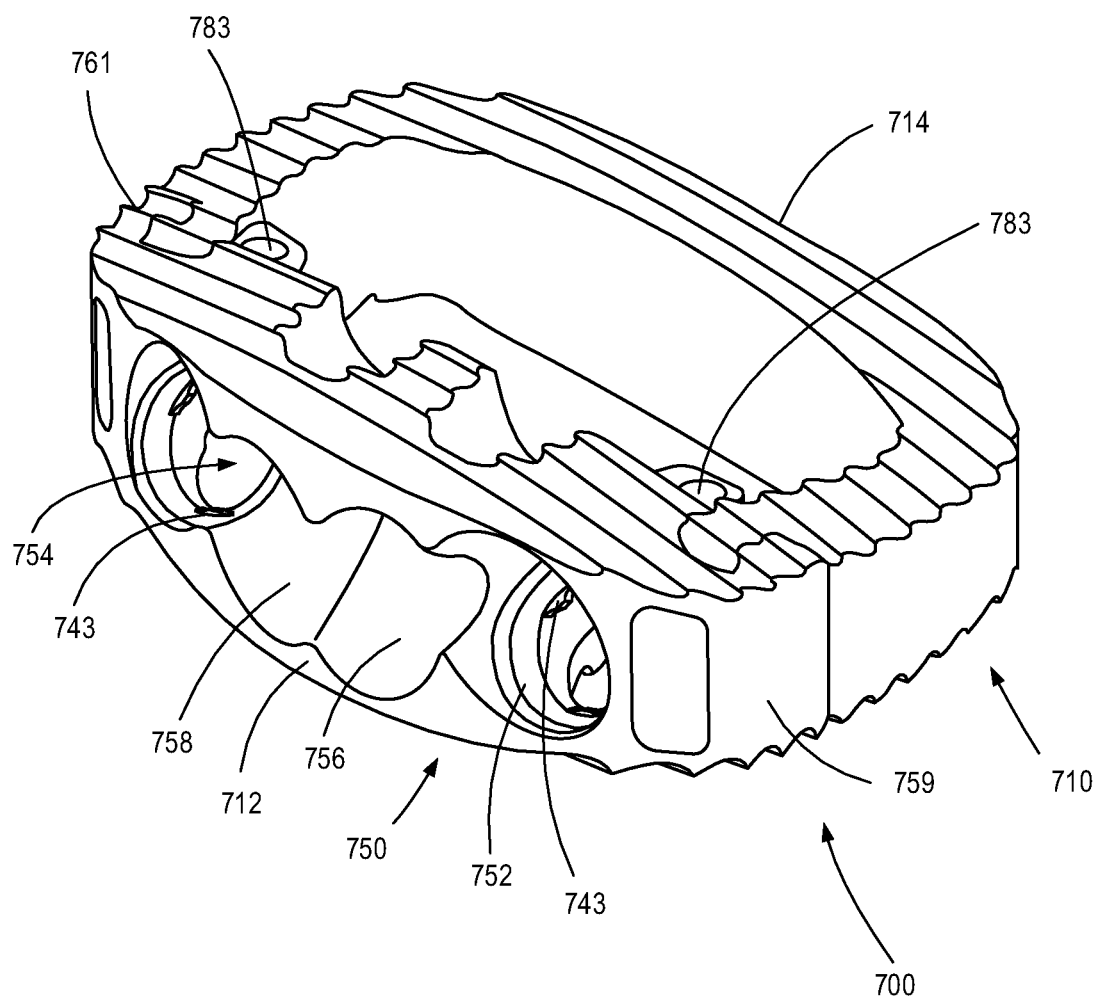
FIG. 8 is a perspective view of the spinal implant of FIG. 7.
Figure 9:
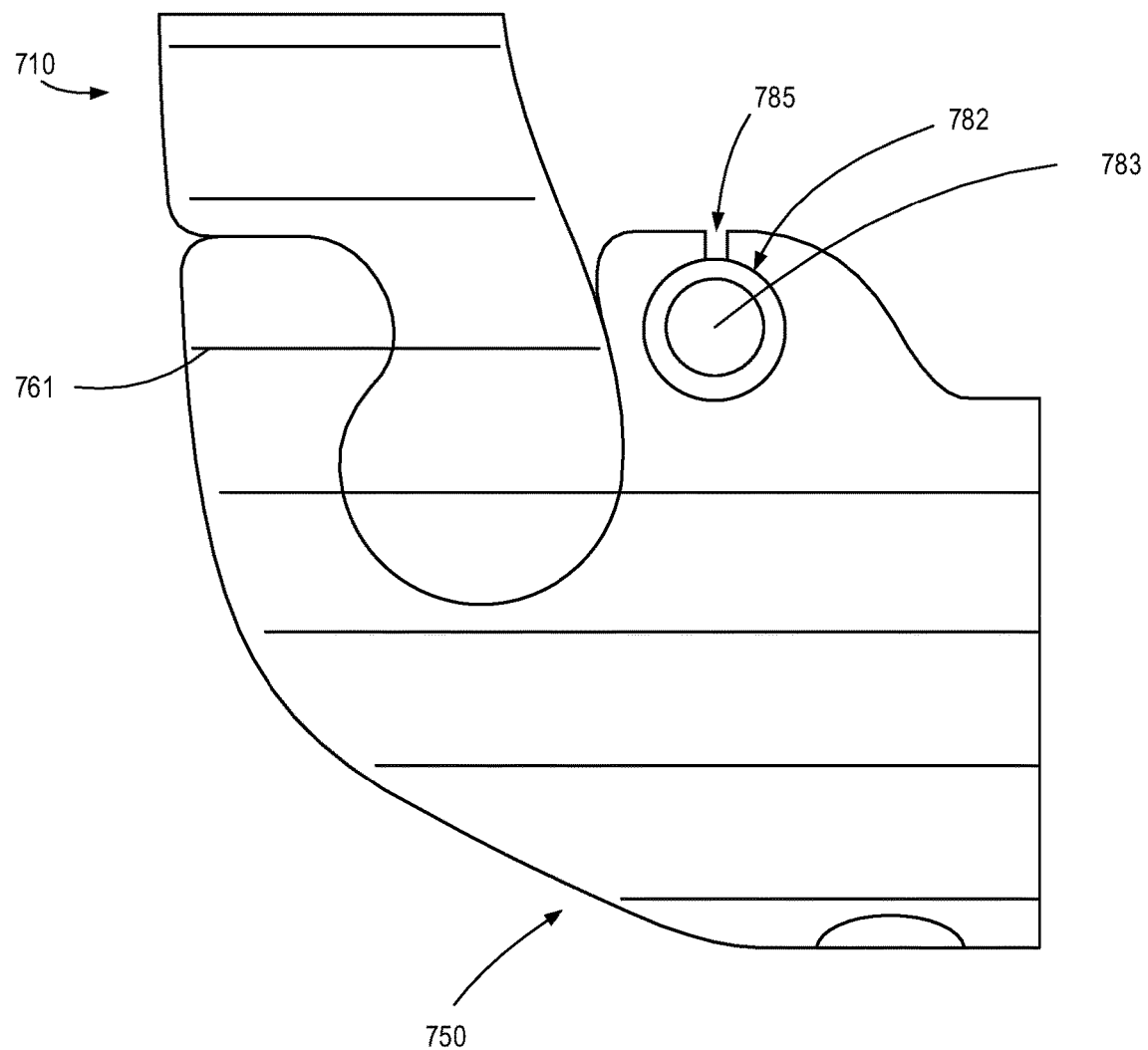
FIG. 9 is a close-up view of one side of a coupling between the base portion and the secondary portion of the spinal implant of FIGS. 7 and 8.

FIGS. 7-9 depict yet another embodiment of a stand-alone ALIF implant 700. Implant 700 is configured to receive four bone screws (not illustrated), two of which are configured to extend through the upper surface 702 and two of which are configured to extend through the lower surface 704. Like implant 600, implant 700 comprises a separate fastener opening for each fastener, namely, fastener openings 752, 754, 756, and 758, and two of these fastener openings overlap. More particularly, fastener openings 756 and 758 overlap.

One or more of fastener openings 752, 754, 756, and 758 may comprise one or more anti-backout features configured to prevent or at least inhibit screws or other fasteners from being removed from these fastener openings once fully positioned therein. For example, as best seen in FIGS. 7 and 8, fastener openings 752 and 754 comprise a plurality of concentrically-positioned protrusions 743. Such protrusions 743 may be configured to engage with corresponding divots, slots, or other recessions formed on a bone screw or other fastener, as discussed in greater detail below. Although not visible in FIG. 7, fastener openings 756 and 758 may also comprise such protrusions if desired.

In alternative embodiments, protrusions 743 may be replaced with similarly-positioned divots, slots, or recessions, and the bone screws/fasteners may instead be formed with protrusions. In this manner, the screws/fasteners may be configured to automatically lock into place at a desired location with the various fastener openings. In some embodiments, this locking may be configured to be audible to allow a surgeon to audibly confirm that the bone screws/fasteners have been adequately locked into place within an implant. As also discussed in greater detail below, in some embodiments, the protrusions and recessions may be configured and arranged so as to only allow for progression of a screw/fastener in one direction and prohibit or at least inhibit reverse threading in the opposite direction. In other words, in some embodiments, the protrusions and recessions may be configured and arranged to allow for a protrusion to exit from one recession and enter an adjacent recession when the screw is advancing into a screw hole, but inhibit/prohibit a protrusion from exiting a current recession in an opposite direction.

Unlike implant 600, base portion 710 of implant 700 lacks a front end wall surface. Instead, the front end wall surface 712 of implant 700 is wholly defined by secondary fastener portion 750. Base portion 710, however, comprises an upper surface 702, a lower surface 704, a first side wall surface 706, a second side wall surface 708 opposite from surface 706, and a rear end wall surface 714.

Like many of the embodiments discussed previously, upper and lower surfaces 702 and 704 both comprise a plurality of engagement structures or teeth 720, which may be arranged in parallel rows that may each extend at least substantially perpendicular to the direction in which side wall surfaces 706 and 708 extend. Upper surface 702 also comprises an opening 722 that also extends through lower surface 704 to allow for ingrowth of bony material therethrough.

Secondary portion 750 further comprises two opposing flanges 759 and 761 that may be configured to be received in corresponding depressions 707 and 709 formed in side wall surfaces 706 and 708 of base portion 710. However, unlike implant 600, implant 700 comprises two opposing locking member openings 780 and 782 positioned along a side of secondary fastener portion 750 opposite from front end wall surface 712. Locking member openings 780 and 782 are configured to receive locking members 783, which in the depicted embodiment comprise locking pins. As best seen in FIG. 9, locking member openings 780 and 782 may comprise slits 784 and 785, respectively, which may allow for some of the material defining locking member openings 780 and 782 to flex upon receiving a locking pin 783 therein. This may allow for locking pins 783 to create a friction fit, snap fit, or otherwise secure base portion 710 in place relative to secondary fastener portion 750, as discussed in greater detail below.

Locking member openings 780 and 782 may be positioned adjacent to respective recesses formed within secondary fastener portion 750. In particular, secondary fastener portion 750 may comprise a first recess 786 positioned adjacent to locking member opening 780 and a second recess 788 positioned adjacent to locking member opening 782. Recesses 786 and 788 may be defined in part by flanges 759 and 761, respectively, as shown in FIGS. 7-9.

Recesses 786 and 788 may be configured to receive at least a portion of the ends of opposing side walls of base portion 710. In some embodiments, an end portion of these side walls may form an enlarged tip, as best seen in FIG. 9. Recesses 786 and 788 may similarly be formed to have a smaller diameter opening and then expand to accommodate this enlarged tip, as also best seen in FIG. 9. Recesses 786 and 788 may therefore accommodate the side wall tips, or another similar portion of base portion 710, in a puzzle-piece or nesting fashion. In some such embodiments, the distal tips of the side walls may be prevented or inhibited from being inserted in recesses 786 and 788 in a horizontal direction (within a plane parallel to upper and/or lower surfaces 702 and 704). In other words, secondary fastener portion 750 may be coupled with base portion 710 by approximating these pieces once positioned vertically or on top of one another.

Alternatively, if slits 784 and 785 are sufficiently wide and/or recesses 786 and 788 are dimensioned appropriately, some embodiments may allow for such coupling in a horizontal direction (or within the same plane). For example, in some embodiments, recesses 786 and 788 may be configured to flex open, due to the presence of slits 784 and 785, to accommodate the side wall tips, or another similar portion of base portion 710, and then flex back into position to prevent these side wall tips from being removed from recesses 786 and 788. These components may then be locked into place by inserting pins 783 or another similar locking member into locking member openings 780 and 782. Pins 783 may be configured to be received in locking member openings 780/782 in a friction-fit manner. Alternatively, pins 783 and/or locking member openings 780/782 may be threaded to facilitate such securement.

It is expected that a variety of alternative embodiments will be apparent to those of ordinary skill in the art after receiving the benefit of this disclosure. For example, alternative embodiments are contemplated in which various elements or components disclosed as formed on a base portion may instead be formed on a secondary portion, and vice versa. For example, in some embodiments, locking member openings may be formed in base portion 710 instead of secondary portion 750. Similarly, recesses 786 and 788 may be formed in base portion 710 rather than secondary portion 750.

Figure 10:
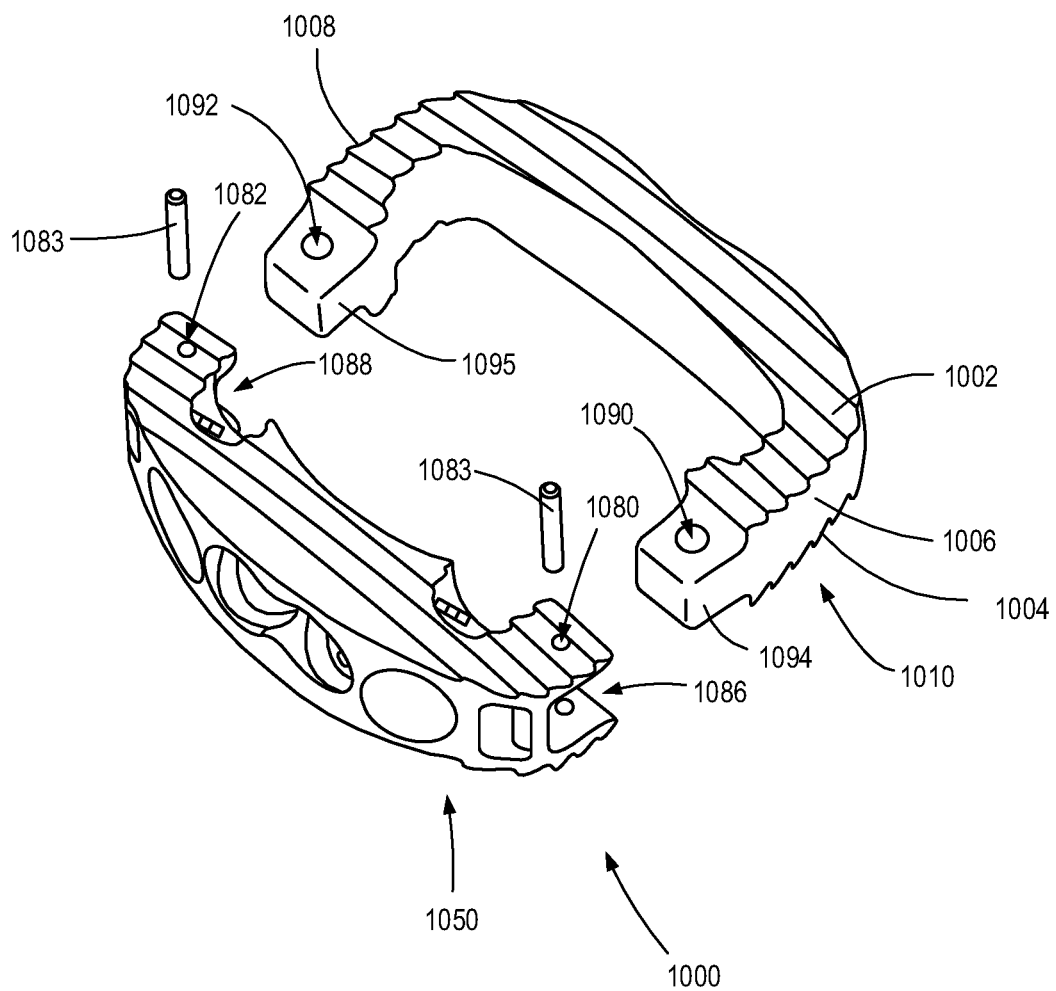
FIG. 10 is an exploded perspective view of yet another embodiment of a stand-alone anterior lumbar interbody fusion spinal implant.
Figure 11:
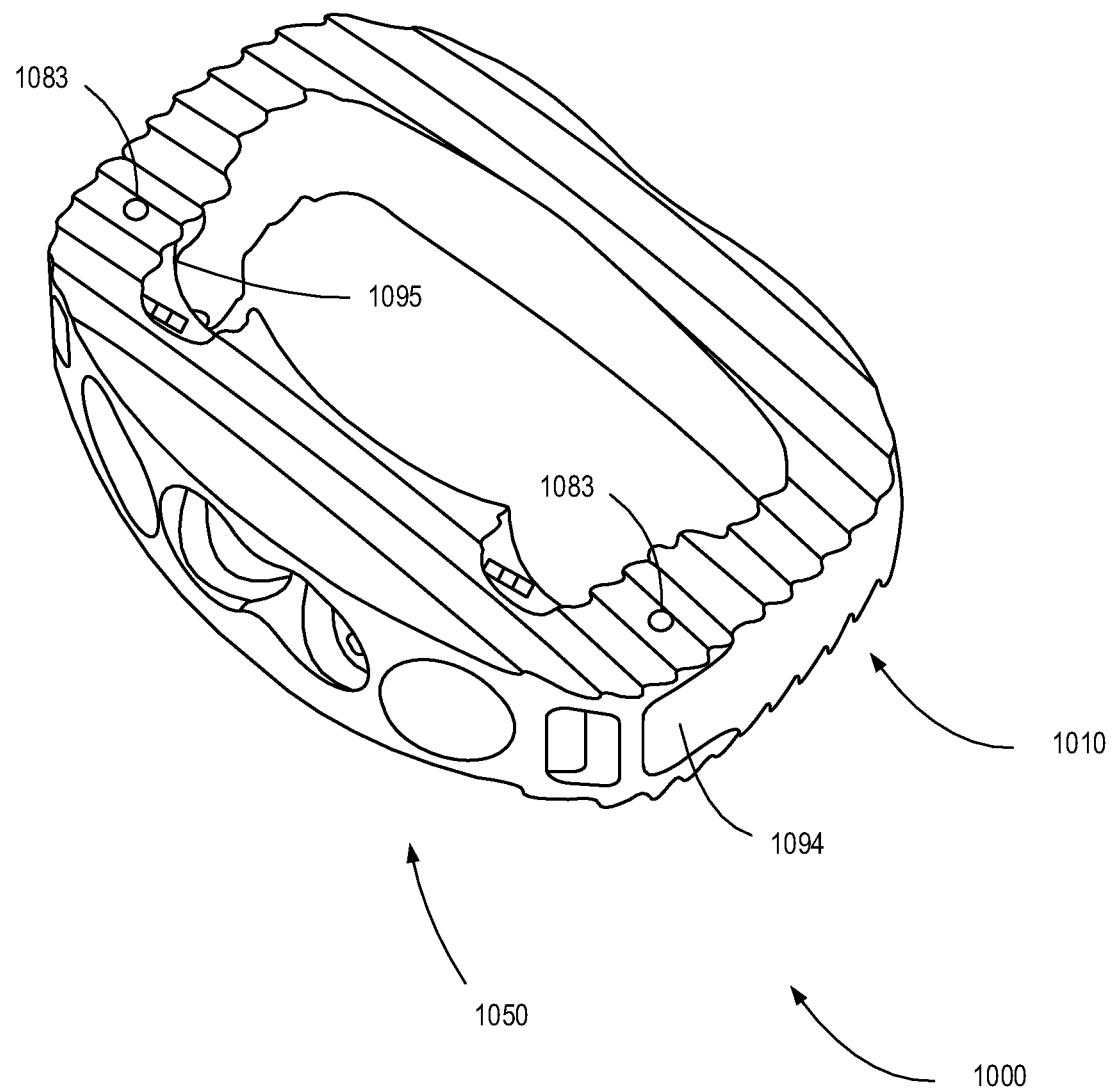
FIG. 11 is a perspective view of the spinal implant of FIG. 10.

FIGS. 10 and 11 depict yet another embodiment of a stand-alone ALIF implant 1000 comprising a base portion 1010 and a secondary fastener portion 1050. Implant 1000 differs from the previously-discussed embodiments in that secondary fastener portion 1050 comprises two opposing recesses 1086 and 1088 that comprise locking member openings 1080 and 1082 configured to receive a pin 1083 or other locking member therethrough. In the depicted embodiment, recesses 1086 and 1088 comprise slits. However, other embodiments are contemplated in which recesses 1086 and 1088 may instead comprise holes formed in secondary fastener portion 1050.

Locking member openings 1080 and 1082 are further configured to be aligned with corresponding locking member openings 1090 and 1092 formed within and extending through tips 1094 and 1095 of side walls 1006 and 1008 of base portion 1010. Tips 1094 and 1095 are narrowed relative to the distance between upper surface 1002 and lower surface 1004 so as to allow for being positioned within recesses 1086 and 1088 without making the upper and lower surfaces of secondary fastener portion 1050 extend a greater distance than upper surface 1002 and lower surface 1004.

Once base portion 1010 is properly positioned relative to secondary fastener portion 1050, pins 1083 may be secured through locking member openings 1080 and 1082, and locking member openings 1090 and 1092 to ensure a secure coupling between base portion 1010 and secondary fastener portion 1050. Pins 1083 may be so secured by a friction fit, for example, or may be threaded. Stand-alone ALIF implant 1000 is otherwise similar to stand-alone ALIF implant 700.

Figure 12:
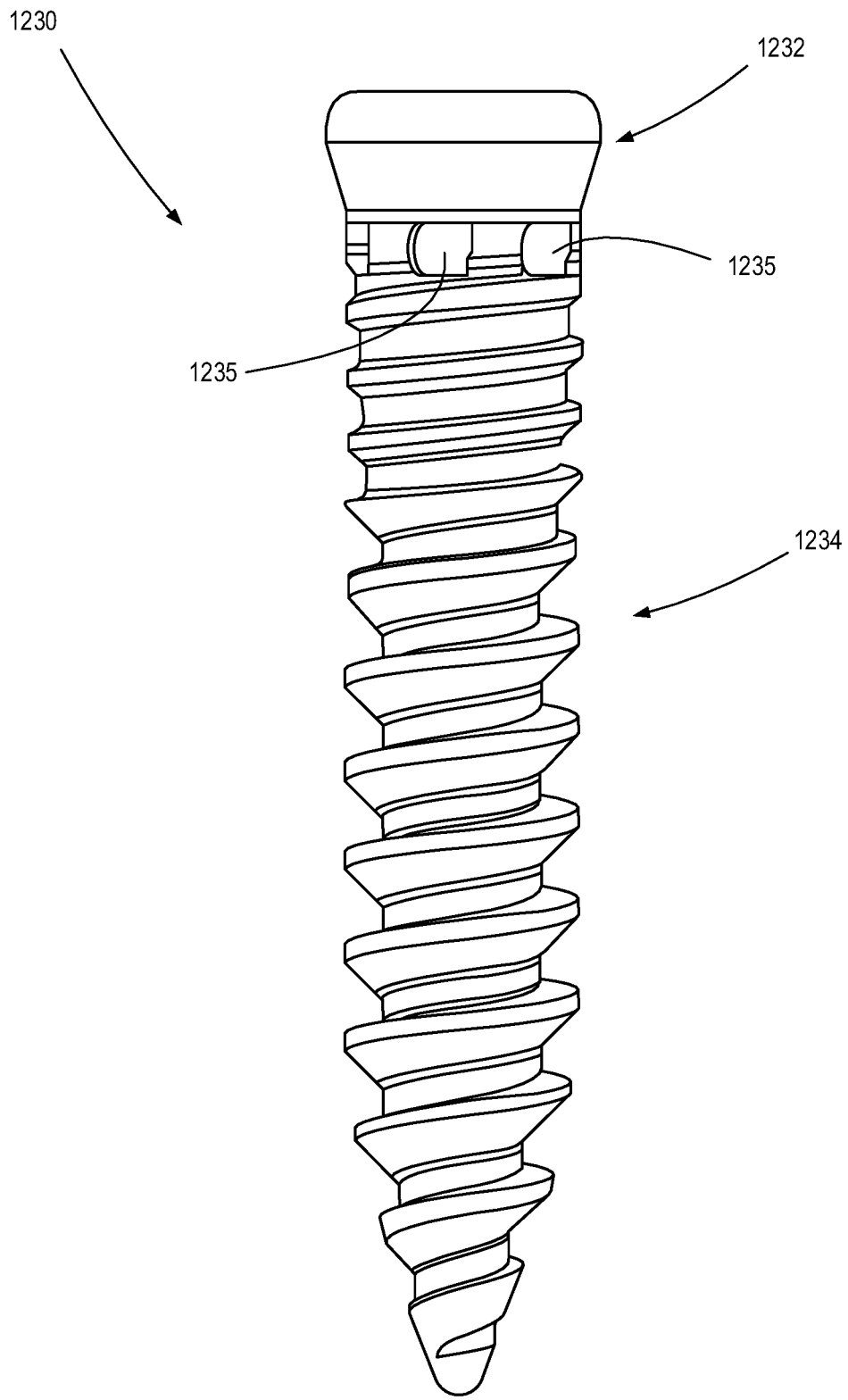
FIG. 12 is an elevation view of an embodiment of a locking screw configured for use with certain embodiments of spinal implants.

FIG. 12 depicts an example of a bone screw 1230 configured for use in connection with one or more of the spinal implants disclosed herein. Bone screw 1230 comprises an unthreaded head 1232 and a threaded section 1234. In the depicted embodiment, threaded section 1234 comprises a variable-pitch thread that comprises threads that are progressively closer together towards unthreaded head 1232. In some embodiments, threaded section 1234 may comprise a variable-pitch thread over the entire length of the threaded section 1234. Alternatively, threaded section 1234 may comprise multiple sub-sections, one or more of which have a constant pitch and one or more of which (preferably near the head 1232) are variable pitch. As another alternative, multiple leads may be used instead of using a single lead with variable pitch. In any event, such variable-pitch, multiple leads, and/or sectioned threads may be useful in creating compression between an intervertebral device and patient bone, which may enhance the anti-backout characteristics of the implant.

Head 1232 may comprise a tapered surface, which may be used to prevent bone screw 1230 from passing all of the way through a corresponding fastener opening in an implant. In some embodiments, head 1232 may therefore taper from a minimum diameter less than a major diameter of the threads of threaded section 1234 to a maximum diameter greater than a major diameter of these threads.

Bone screw 1230 further comprises a plurality of recessions 1235 positioned about a proximal portion of threaded section 1234. As previously mentioned, recessions 1235 may be configured to engage corresponding protrusions formed within a fastener opening of a spinal implant or other biomedical implant. In alternative embodiments, recessions 1235 may be positioned about an unthreaded section of bone screw 1230. For example, in some embodiments, recessions 1235 may be positioned about unthreaded head 1232 rather than about a proximal portion of threaded section 1234.

Figure 13:
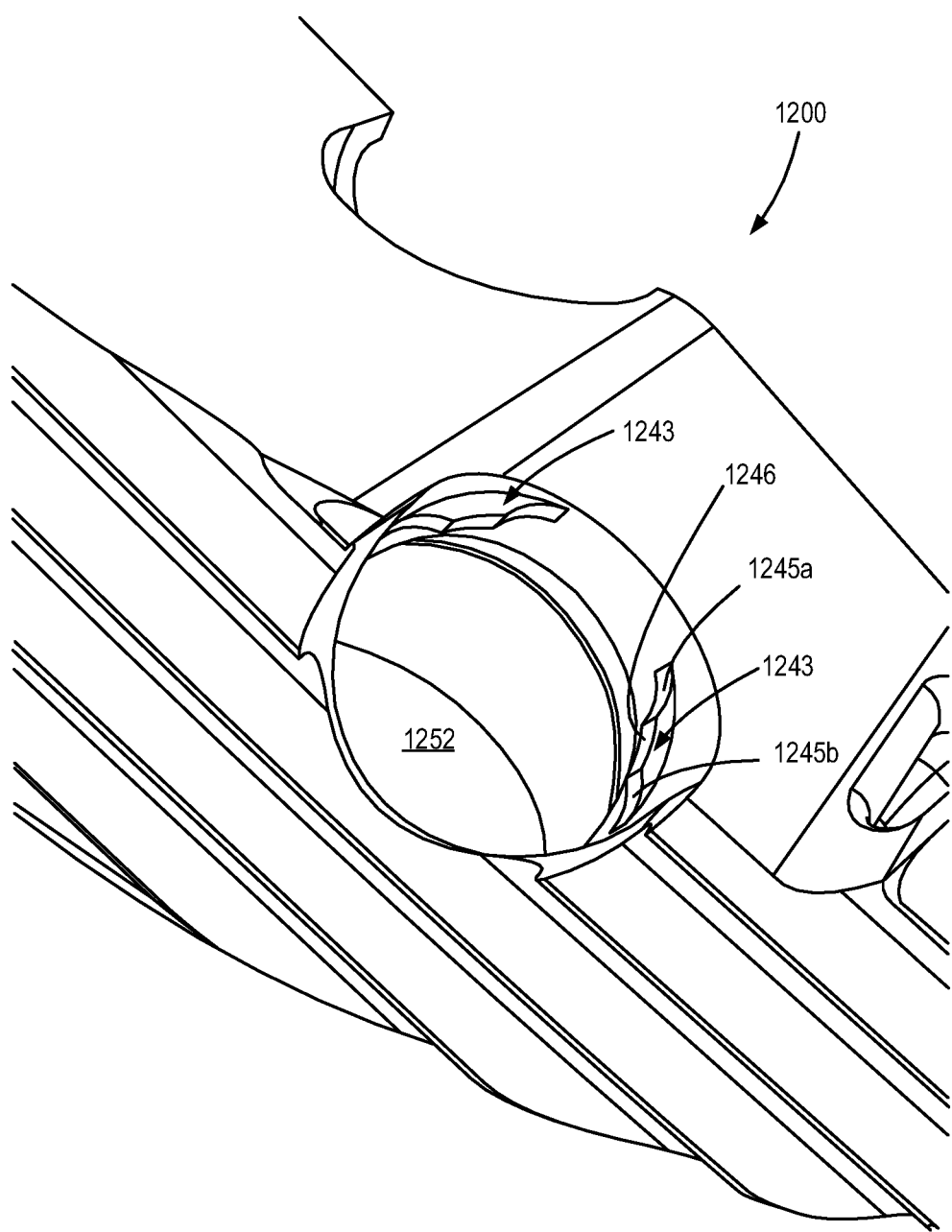
FIG. 13 is a close-up perspective view of a fastener opening of a spinal implant comprising locking features configured for engaging a corresponding locking fastener.

FIG. 13 depicts a close-up view of a fastener opening 1252 of a spinal implant 1200. One or more other similar openings (not shown in this figure) may also be included if desired. As shown in FIG. 13, fastener opening 1252 comprises a plurality of protrusions 1243 positioned along a surface defining fastener opening 1252. Protrusions 1243 may be defined by a two opposing ramped surfaces, namely, ramped surfaces 1245a and 1245b. Ramped surfaces 1245a and 1245b may both lead to a central portion 1246 of protrusion 1243. In some embodiments, central portion 1246 may comprise a flat surface, or an at least substantially flat surface. In some embodiments, ramped surfaces 1245a and 1245b may comprise concave surfaces. Alternatively, ramped surfaces 1245a and 1245b may comprise flat surfaces positioned at an angle with respect to central portion 1246 so as to facilitate desired positioning of protrusions 1243 within respective recessions, such as recessions 1235, of a bone screw or other fastener.

In some preferred embodiments, protrusions 1243 may be arranged in a helical pattern about a surface defining fastener opening 1252, as shown in FIG. 13. This helical pattern may be configured to match, or at least substantially match, a corresponding helical pattern of threads of a bone screw, such as bone screw 1230. Although some embodiments are contemplated in which recessions 1235 may similarly be placed about bone screw 1230 in a helical pattern, in certain preferred embodiments recessions 1235 are not placed in a helical pattern. Instead, recessions 1235 may be placed in a circular pattern about the same portion (i.e., same position along the axis of bone screw 1230) of bone screw 1230.

In addition, in some preferred embodiments, protrusions 1243 may be configured to taper, again, to match the taper of a screw, according to their positioning depth within fastener opening 1252. More particularly, in certain preferred embodiments, the height of protrusions 1243 (measured from the wall defining fastener opening 1252) may increase from the proximal portion of a particular fastener opening 1252 to the distal portion of the fastener opening 1252. In some embodiments, this taper of the helical protrusions may be configured to match, or at least substantially match, the taper of a minor diameter of an associated screw, such as bone screw 1230. In this manner, bone screw 1230, or another similar fastener, may be configured to allow for rotation of bone screw 1230 within fastener opening 1252 once at least one of protrusions 1243 has engaged a corresponding recession 1235 in a particular direction, but prevent, or at least inhibit, rotation of bone screw 1230 in an opposite direction. This may be used to prevent, or at least inhibit, unwanted backout of bone screw 1230.

In some embodiments, one or more (in some cases, all) of protrusions 1243 may comprise a width (measured in a direction perpendicular to, or at least substantially perpendicular to, the direction in which ramped surfaces 1245a and 1245b extend and/or parallel to, or at least substantially parallel to, the direction in which bone screw 1230 extends into a fastener opening 1252) that is less than a pitch of bone screw 1230 (or at least a particular pitch of bone screw 1230 in the region in which recessions 1235 are positioned).

However, it may be preferable, depending upon the positioning of recessions 1235, to create recessions 1235 such that they comprise a height (measured along the axis of bone screw 1230) that is substantially greater than the width (as described above) of protrusions 1243. This may allow for multiple protrusions 1243 to be simultaneously positioned within multiple respective recessions 1235. In some embodiments, one or more (in some cases, all) of the recessions 1235 may comprise a height that is no greater than twice the pitch of the threads at or near the location of the recessions 1235. In some embodiments, the recessions 1235 may be configured and positioned so as to avoid crossing more than one thread crest. However, other embodiments are contemplated in which the height may be greater than this length, particularly if the recessions extend beyond the extent of the threads, such as on or towards the unthreaded head 1232 of the bone screw 1230.

Although, as mentioned above, in certain preferred embodiments, protrusions 1243 may be arranged in a tapered and/or helical manner about fastener opening(s) 1252, in some embodiments, each of the protrusions 1243 may themselves not be arranged in this manner. In other words, the protrusions 1243 may be positioned to extend parallel to, or at least substantially parallel to, a perimeter of fastener openings(s) 1252 such that each individual protrusion 1243 does not itself taper inwardly, despite the fact that the placement of the protrusions 1243 results in a collective taper inwardly within a particular fastener opening 1252. This may be useful in order to further facilitate a desired anti-backout effect by creating an interference fit between one or more of the protrusions 1243 and one or more respective recessions 1235.

It is contemplated that, in some alternative embodiments, the protrusions may instead be positioned on a bone screw or other fastener and the recessions may be positioned about a fastener opening. However, it is thought that the preferred embodiments disclosed herein wherein the protrusions are positioned in a tapered helical manner about fastener opening(s) 1252 and recessions are positioned about a proximal portion of bone screw(s) 1230 may be preferred for certain applications.

Figure 14:
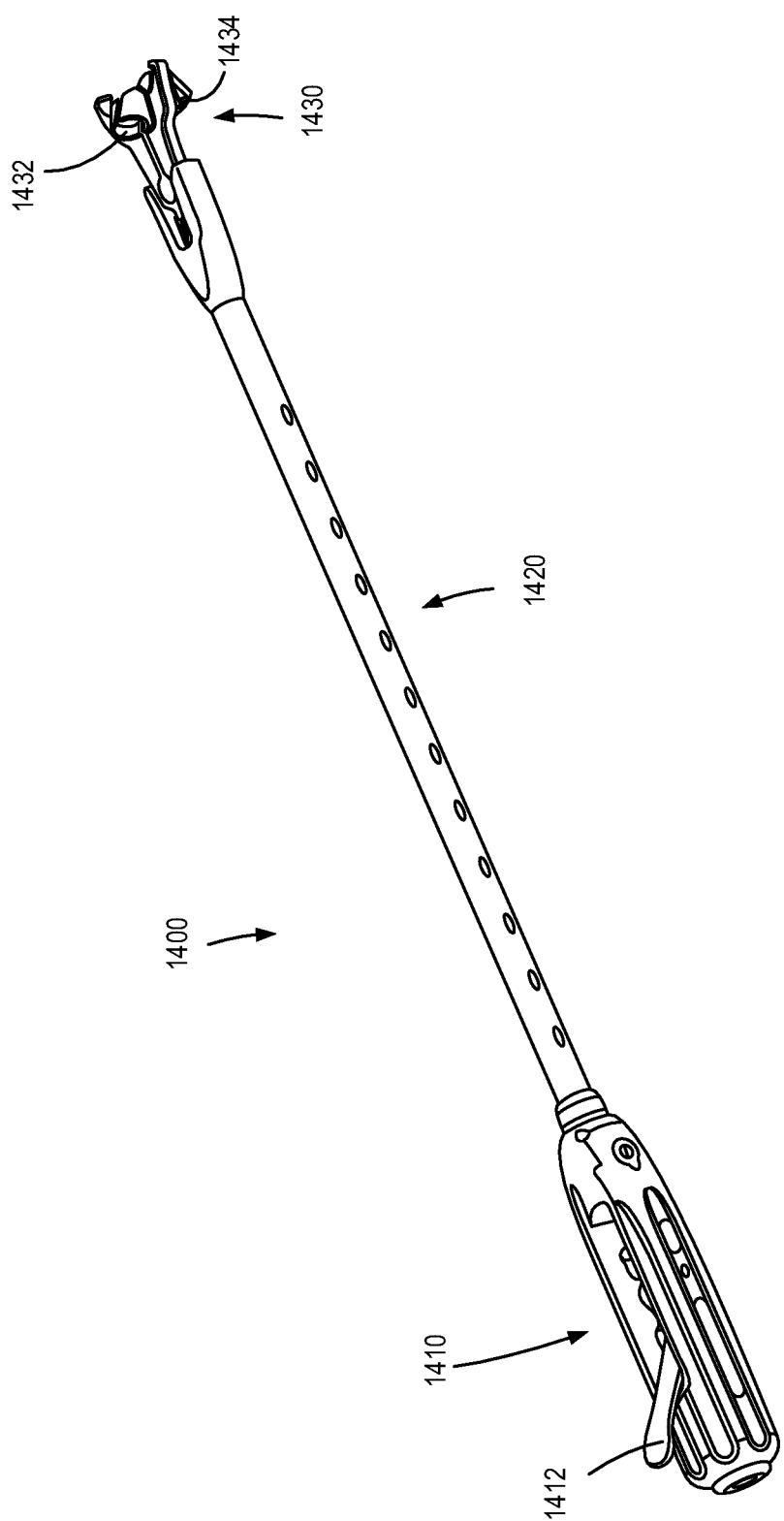
FIG. 14 is a perspective view of an embodiment of an inserter tool that may be used to install screws and/or fasteners into one or more of the spinal implants disclosed herein.

FIG. 14 depicts an embodiment of an inserter tool 1400 that may be used to insert one or more of the implants disclosed herein and/or install screws and/or fasteners into one or more of the implants disclosed herein. Inserter 1400 comprises a handle 1410, a shaft 1420, and a tip 1430. Handle 1410 comprises a lever 1412 configured to lock tip 1430 in place. In some embodiments, tip 1430 may be replaced by a variety of other tips having different shapes and sizes such that a single inserter 1400 may be used in connection with an entire collection of standalone ALIF implants or other spinal implants. Thus, lever 1412 may be configured such that in one position, tip 1430 is secured in place and in a second position, lever 1412 releases tip 1430 to allow for a different tip to be used with tool 1400.

Tip 1430 comprises two fastener holes, namely fastener hole 1432 and fastener hole 1434. Hole 1432 is configured to be coupled with a corresponding fastener opening of a spinal implant to facilitate placement of bone screws or other fasteners within the fastener opening. Similarly, hole 1434 is configured to be coupled with another corresponding fastener opening of the same spinal implant to facilitate placement of bone screws or other fasteners within the fastener opening. As illustrated in FIG. 14, hole 1432 is positioned on one side of inserter 1400 and hole 1434 is positioned on an opposite side of inserter 1400. Holes 1432 and 1434 are also angled in opposite directions such that hole 1432 can be aligned and coupled with a fastener opening configured to deliver a bone screw into a first vertebral bone and hole 1434 can be aligned and coupled with a fastener opening configured to deliver a second bone screw into a second vertebral bone, as described above in connection with various embodiments of standalone ALIF implants. Holes 1432 and 1434 may be further configured to be coupled with (in some embodiments, fixedly engage) a guide tube configured to deliver the bone screws or other fasteners through holes 1432 and 1434 and, ultimately, into fastener openings of a spinal implant, as described in greater detail below.

Figure 15:
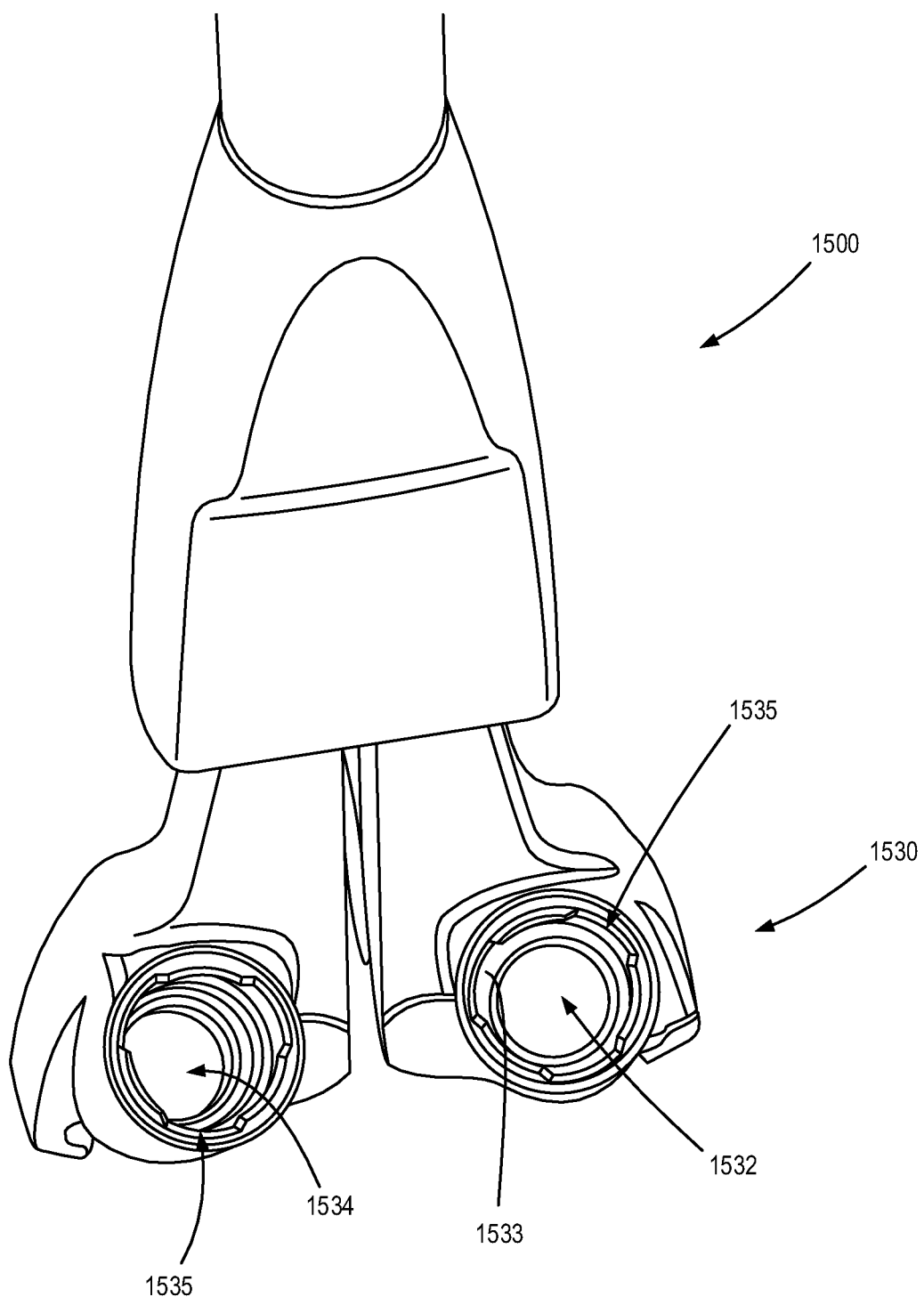
FIG. 15 is a close-up view of a distal tip of another embodiment of an inserter tool.

Of course, a wide variety of alternative tips are contemplated having varying numbers, angles, and positions for the fastener holes. For example, FIG. 15 illustrates a close-up view of a tip 1530 of an alternative embodiment of an inserter tool 1500. Tip 1530 comprises two adjacent fastener holes 1532 and 1534, both of which are positioned on the same side of inserter 1500 and both of which are angled in the same manner so as to be angled towards the same vertebral body during surgery. In some embodiments, another two fastener holes (not shown in FIG. 15) may be positioned on the opposite side so as to facilitate delivery of bone screws or other fasteners into a different vertebral body. Such an embodiment may be used, for example, in connection with stand-alone ALIF implant 600 of FIG. 6.

Fastener holes 1532 and 1534 further comprise locking features configured to facilitate a secure connection between inserter 1500 and one or more corresponding guide tubes (discussed in greater detail below). More particularly, fastener holes 1532 and 1534 both comprise an internal channel 1533 positioned in between the top and bottom peripheral openings defining holes 1532 and 1534. Holes 1532 and 1534 further comprise a plurality of slots 1535 defined within the holes such that channel 1533 is exposed only in the areas of holes 1532 and 1534 where slots 1535 are positioned. This may allow for a guide tube having a similar plurality of tabs positioned on an exterior surface to be locked into position by aligning the tabs with the slots 1535 and then rotating the guide tube, as discussed in greater detail below.

Of course, a variety of alternative embodiments are contemplated. For example, although fastener holes 1532 and 1534 are shown as having three slots 1535 positioned evenly about these holes, other numbers and positions of such slots 1535 may be used as desired. In addition, in a specific alternative configuration for facilitating a secure coupling between a guide tube and an inserter instrument, the guide tube may lack slots 1535. In such embodiments, the guide tube may comprise a single tab or ridge, or multiple tabs/ridges, and may be configured with one or more slits in the end of the guide tube (in some embodiments, two slits positioned 180 degrees from each other). This may allow the tube to be contracted and fit within a fastener hole of an inserter tool and then expanded within the fastener hole such that the tab(s) can enter the channel.

Figure 16:
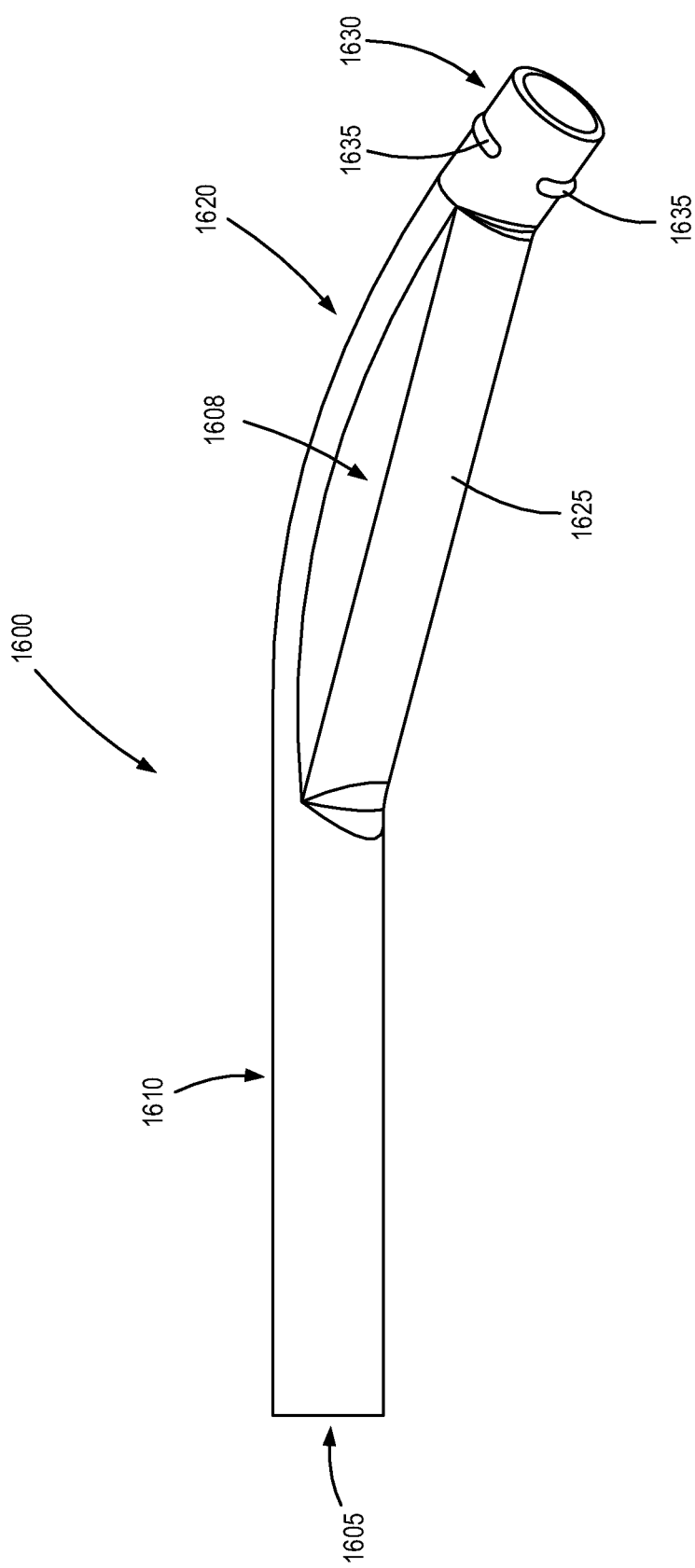
FIG. 16 is a perspective view of a distal end of an embodiment of a guide tube that may be used in connection with an inserter tool to install screws and/or fasteners into one or more of the spinal implants disclosed herein.

FIG. 16 depicts a distal end of an embodiment of a guide tube 1600 that may be used to install one or more of the implants described herein and may also be used in connection with one or more of the inserter tools described herein. Guide tube 1600 comprises a lumen 1605 defined by a shaft comprising a distal portion 1620 that is angled with respect to a primary portion 1610 of the guide tube 1600 shaft. In some embodiments, the angle with which distal portion 1620 extends relative to primary portion 1610 may at least substantially correspond with an angle that a fastener opening of a spinal implant extends relative to an axis of the implant, such as an axis defined by the top and/or bottom surface of the implant. However, in other embodiments, this need not be the case.

For example, in some embodiments, the angle with which distal portion 1620 extends relative to primary portion 1610 may be greater than the angle of angle that a fastener opening of a spinal implant extends relative to an axis of the implant. This may be useful to allow for providing a greater degree of clearance between guide tube 1600 and inserter 1500 to prevent the two instruments from interfering with one another during a surgical procedure. In some embodiments, this angle may result in a projection of the axis of guide tube 1600 crossing a projection of the axis of inserter 1500 such that the proximal portion of guide tube 1600 extends away from the proximal portion of inserter 1500 to allow for additional room between the instruments at the respective proximal ends.

Guide tube 1600 further comprises a hood 1625 positioned along at least a portion of the distal portion 1620 of guide tube 1600. Hood 1625 may be used to cover an expanded region 1608 of the lumen 1605 of guide tube 1600. Expanded region 1608 may be provided to allow for one or more bone screws or other fasteners to extend through the angled distal portion 1620 of guide tube 1600. Hood 1625 may be used to prevent the screws from exiting guide tube 1600 in this region. Hood 1625 is substantially coincident with angled distal portion 1620 of the shaft of guide tube 1600 in the depicted embodiment. However, other embodiments are contemplated in which hood 1625 is positioned along less of angled distal portion 1620. This variable may depend upon the angle between distal portion 1620 and primary portion 1610. In the depicted embodiment, hood 1625 completely encloses expanded region 1608. However, other embodiments are contemplated in which hood 1625 only partially encloses expanded region 1608.

Guide tube 1600 further comprises a tip 1630 comprising a plurality of tabs 1635 corresponding with the plurality of slots 1535 positioned within fastener holes 1532 and 1534 of inserter tool 1500. Guide tube 1600 may be coupled with a particular fastener hole by aligning tabs 1635 with slots 1535, approximating guide tube 1600 with inserter tool 1500 to insert tabs 1635 into slots 1535, and then rotating guide tube 1600 with respect to inserter tool 1500 to allow tabs 1635 to enter channel 1533 and lock guide tube 1600 in place.

In alternative embodiments, guide tube 1600 may be snap-fit into place. For example, in some embodiments, tabs 1635 may instead comprise a single tab or protrusion, which may extend all of the way around a perimeter of tip 1630. Such embodiments may comprise one or more slits positioned in the end of tip 1630, which may allow the distal end of the guide tube to flex and fit within a fastener hole of an inserter tool, such as fastener holes 1532 and 1534 of inserter tool 1500, after which the guide tube may be expanded within the fastener hole such that the tab/protrusion can enter channel 1533 without requiring a particular rotational orientation. In some preferred embodiments, tip 1630 may comprise two such slits positioned opposite (at or about 180 degrees) from one another.

Figure 17:
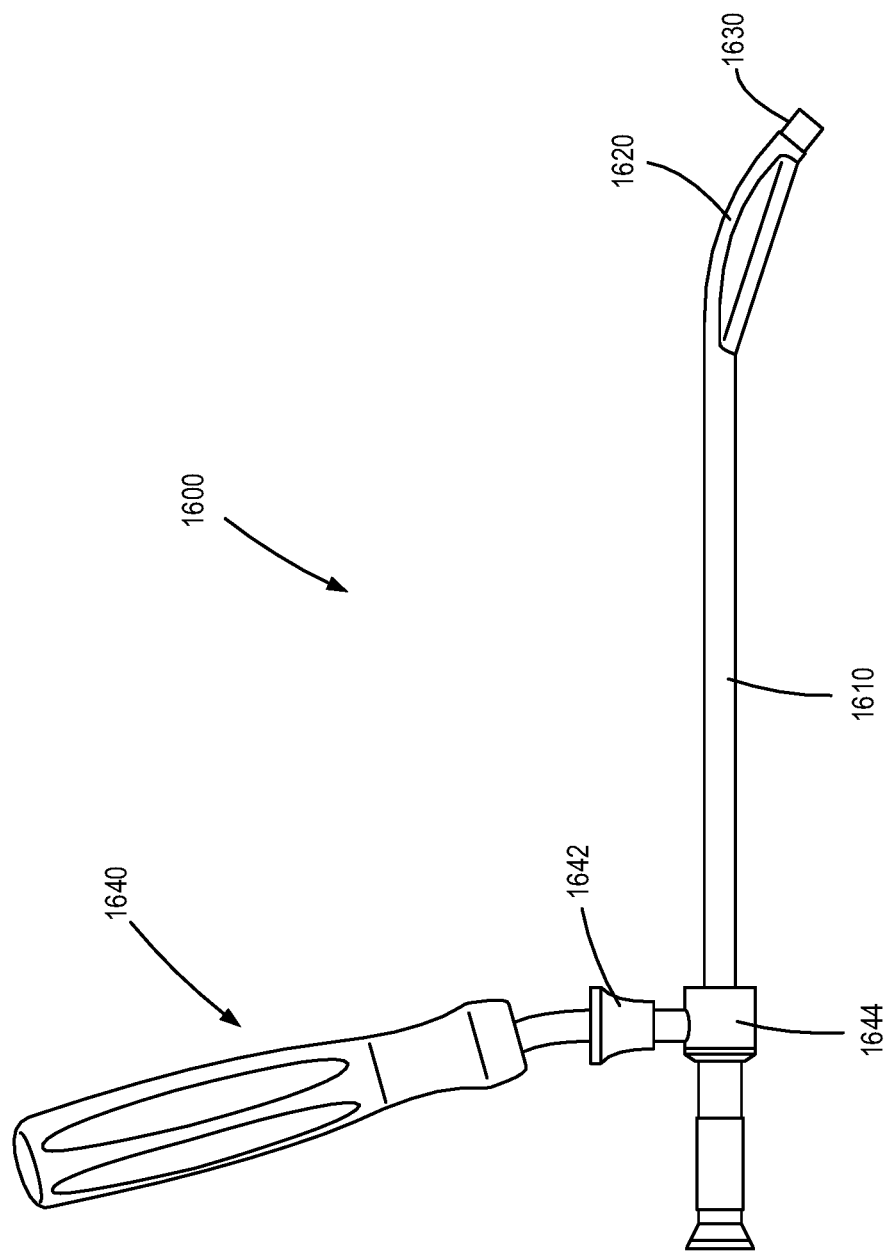
FIG. 17 is a perspective view of the entire guide tube of FIG. 16.

FIG. 17 depicts a perspective view of the entire guide tube 1600. As shown in this figure, guide tube 1600 further comprises a handle 1640. Handle 1640 comprises a collar 1642 that may be used to reposition handle 1640 with respect to the shaft of guide tube 1600. More particularly, a user may pull back on collar 1642, rotate handle 1640 to a desired position relative to the shaft of guide tube 1600, and then release collar 1642 to lock handle 1640 in place. Collar 1642 is coupled to a handle hub 1644, which may comprise elements used to allow for such repositioning, such as a ratchet mechanism, a ball joint, a clutch mechanism, or the like.

It can also be seen in FIG. 17 that handle 1640 initially extends at an at least substantially perpendicular angle relative to the shaft of guide tube 1600 and then angles upward slightly relative to this perpendicular direction. This may provide for a more ergonomic feel for guide tube 1600. In some embodiments, this angle, like the rotational position of handle 1640, may also be adjustable.

In some embodiments, guide tube 1600 may be configured to be directly coupled with an implant without use of an inserter. For example in some embodiments, the implant fastener openings may be configured to directly receive the distal end of a guide tube by way of a friction fit, or one of the other locking coupling features disclosed above relative to the inserter 1500, such as slots 1535 and tabs 1635, for example. In still other embodiments, the guide tube may comprise multiple lumens each configured to engage with a separate opening, either of an inserter tool or an implant directly, and drive a separate fastener therethrough, either simultaneously or sequentially. In some such embodiments, a single lumen at a proximal end of the guide tube may split into multiple lumens at the distal end.

Some embodiments may be configured to have one or more screws/fasteners pre-loaded within one or more of the guide tube lumens. For example, in some embodiments, one or more resiliently deformable features may be formed adjacent to a distal opening of the guide tube. Such features may be used to keep the pre-loaded screws/fasteners in the guide tube until sufficient force, such as may be provided by a driver tool, is used to deform these components to allow them to fully pass through the distal opening of the guide tube.

In some embodiments, the guide tube may be directly coupled with only a subset (rather than all, as discussed above) of the fastener openings of an implant or inserter. Thus, for example, a subset of fastener openings of an implant may be more difficult to access. Such fastener opening(s) may have a direct and/or permanent coupling with a guide tube or the guide tube may have a direct and/or permanent coupling with an inserter. Other fastener openings that are more easily accessible may then be accessed by a different guide tube.

Figure 18:
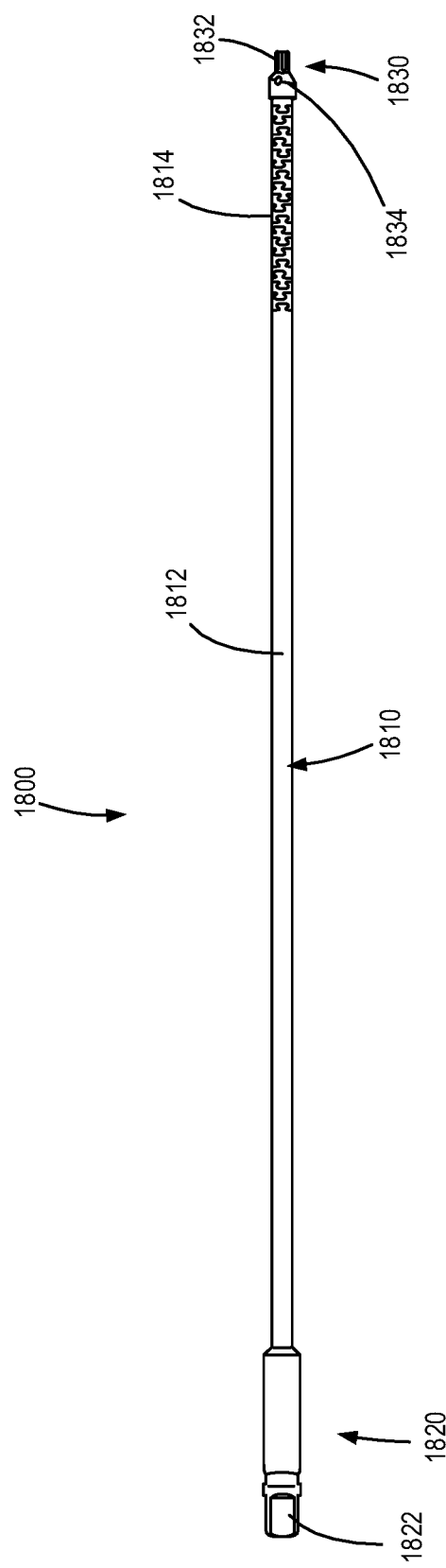
FIG. 18 is a perspective view of an embodiment of a flexible driver instrument that may be used in connection with one or more of the guide tubes and/or inserter tools disclosed herein to install screws and/or fasteners into one or more of the spinal implants disclosed herein.

FIG. 18 depicts an embodiment of a driver 1800 that may be used to install one or more of the implants described herein and may also be used in connection with one or more of the inserter tools and/or guide tubes described herein during such procedures. Driver 1800 comprises a shaft 1810, a proximal tip 1820, and a distal tip 1830. Shaft 1810 comprises a relatively rigid section 1812 and a flexible section 1814. Flexible section 1814 is configured to allow for shaft 1810 to flex within guide tube 1600. More particularly, in the depicted embodiment, flexible section 1814 is specifically configured to allow for flexing of shaft 1810 within the region of distal portion 1620 of guide tube 1600. Thus, in some preferred embodiments, flexible section 1814 may have a length that is at least substantially equal to a length of an angled portion of a guide tube (such as distal portion 1620 of guide tube 1600).

In the depicted embodiment, flexible section 1814 is created by cutting a series of cuts, such as laser cuts for example, that may extend circumferentially around the outer surface of the flexible section 1814 to enhance flexibility. In some embodiments, the cuts may score the outer surface or flexible section 1814. Alternatively, the cuts may extend all of the way through a wall of flexible section 1814 to a hollow interior. In such embodiments, the cuts may form discrete portions that may interlock due to the shape of the cuts. In the depicted embodiment, for example, the cuts may be formed in the shape of interlocking puzzle pieces.

Proximal tip 1820 comprises a keyed section 1822 configured to engage a tool for providing a torsional force to driver 1800 to drive bone screws or other fasteners through an implant and, in some embodiments, into a patient's bone, such as into vertebral bodies of a patient's spine. Distal tip 1830 similarly comprises a keyed section 1832 configured to engage a bone screw or other fastener. Adjacent to keyed section 1832, distal tip 1830 further comprises an expanded region 1834. Expanded region 1834 may be used to keep driver 1800 centered within guide tube 1600, which may help keep a desired trajectory for bone screws or other fasteners being driven within guide tube 1600. In the depicted embodiment, expanded region 1834 comprises a bulb. However, other embodiments are contemplated in which expanded region 1834 instead comprises one or more protrusions configured to engage an inside wall of the lumen of guide tube 1600.

In some embodiments, two or more of the instruments disclosed herein may be combined into a single instrument. For example, the driver may be coupled with the guide tube in such a way that a single instrument is used for both functions, as described in greater detail below. Similarly, in some embodiments, the guide tube and inserter may be combined into a single instrument. Alternatively, the driver, guide tube, and inserter may all three be combined into a single instrument.

Figure 19:
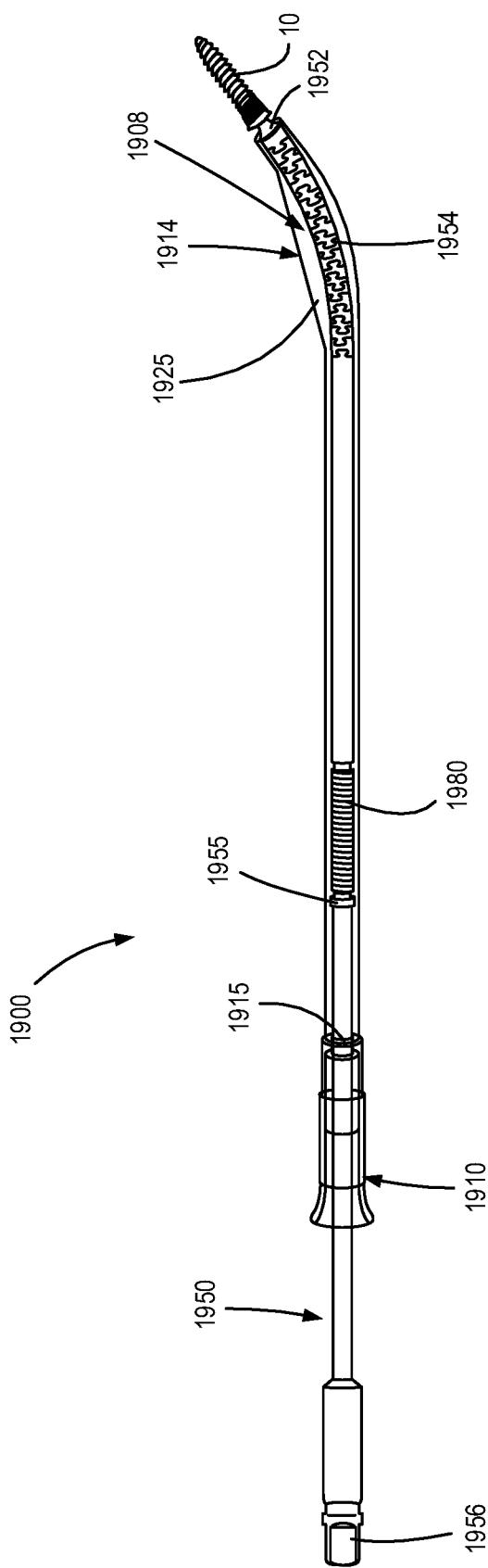
FIG. 19 is a phantom, perspective view of an embodiment of an instrument comprising a combined guide tube and flexible driver.

An example of one such combined instrument is shown in the phantom, perspective view of FIG. 19, which depicts an embodiment of a surgical instrument 1900 comprising a combined guide tube and flexible driver.

Instrument 1900 comprises a guide tube 1910 and a flexible driver 1950 positioned within the guide tube 1910. In the depicted embodiment, flexible driver 1950 is positioned within guide tube 1910 such that flexible driver 1950 cannot be fully withdrawn from guide tube 1910, and such that guide tube 1910 and flexible driver 1950 are components of a single instrument, rather than separate instruments that may be used together.

This may be accomplished in a number ways, as those of ordinary skill in the art will appreciate. However, in the depicted embodiment, this is accomplished by providing one or more collars or other expanded regions, such as collar 1955, that are positioned on selected portions of the driver 1950. Collar 1955 may be configured to engage a corresponding shelf, such as shelf 1915, on guide tube 1910, so as to confine driver 1950 within guide tube 1910. A similar shelf or other retention feature may be positioned at an opposite end of the guide tube to engage another collar or other such retention feature on the driver if desired to retain the driver within a particular region of the guide tube. However, as discussed above, other embodiments are contemplated in which these components are instead separate instruments that may be used together in certain implementations of inventive methods disclosed herein.

Surgical instrument 1900 further comprises a spring 1980. Spring 1980, or another similar means for spring loading driver 1950 with respect to guide tube 1910, may be used to bias driver 1950 in a particular direction relative to guide tube 1910. For example, in the depicted embodiment, spring 1980 biases driver 1950 towards the position depicted in FIG. 20, which depicts instrument 1900 in a retracted position with a bone screw 10 retracted into the guide tube 1910 portion of the combined instrument 1900.

Bone screw 10, or another such fastener, may be coupled with a distal end of driver 1950 by way of a tapered "stick-fit" on the driver tip 1952 or some other retention feature or features. Thus, in use, driver 1950 may be advanced distally relative to guide tube 1910 such that driver tip 1952 extends out of the distal opening of guide tube 1910. In some embodiments, driver tip 1952 may comprises a keyed section configured to facilitate engagement with a bone screw or other fastener, as previously discussed. After being coupled with a bone screw or other fastener, driver 1950 may be retracted relative to guide tube 1910 such that driver tip 1952 and/or bone screw 10 are at least partially (in some cases, fully) retracted within a lumen of guide tube 1910. Once the distal end of guide tube 1910 has been coupled with a fastener opening of an implant, such as a stand-alone anterior lumbar interbody fusion spinal implant, driver 1950 may be used to advance (in some cases, by rotation of driver 1950) bone screw 10 into the fastener opening and, ultimately, into a vertebral body of a patient's spine.

In some embodiments, one or more bone screws or other fasteners may be pre-loaded within the lumen of guide tube 1910. For example, in some embodiments, one or more resiliently deformable features may be formed adjacent to a distal opening of guide tube 1910. Such features may be used to keep the pre-loaded bone screw 10 in the guide tube until sufficient force is used to deform these components to allow bone screw 10 to fully pass through the distal opening of guide tube 1910. Preferably, the features/components used to keep bone screw 10 within guide tube 1910 are sufficient to prevent the force of spring 1980 alone from advancing bone screw 10 out of guide tube 1910.

As also previously described, driver 1950 may comprise a flexible section 1954, which may be used to facilitate advancement of a bone screw or other fastener though an angled portion 1914 of guide tube 1910. Driver 1950 may further comprise a proximal tip 1956, which, as described above, may comprise a keyed section configured to engage a tool for providing a torsional force to driver 1950 to drive bone screws or other fasteners through an implant and, in some embodiments, into a patient's vertebrae or other bone structure. In some embodiments, instrument 1900 may comprise a drill or awl to further facilitate such driving of bone screws.

Figure 20:
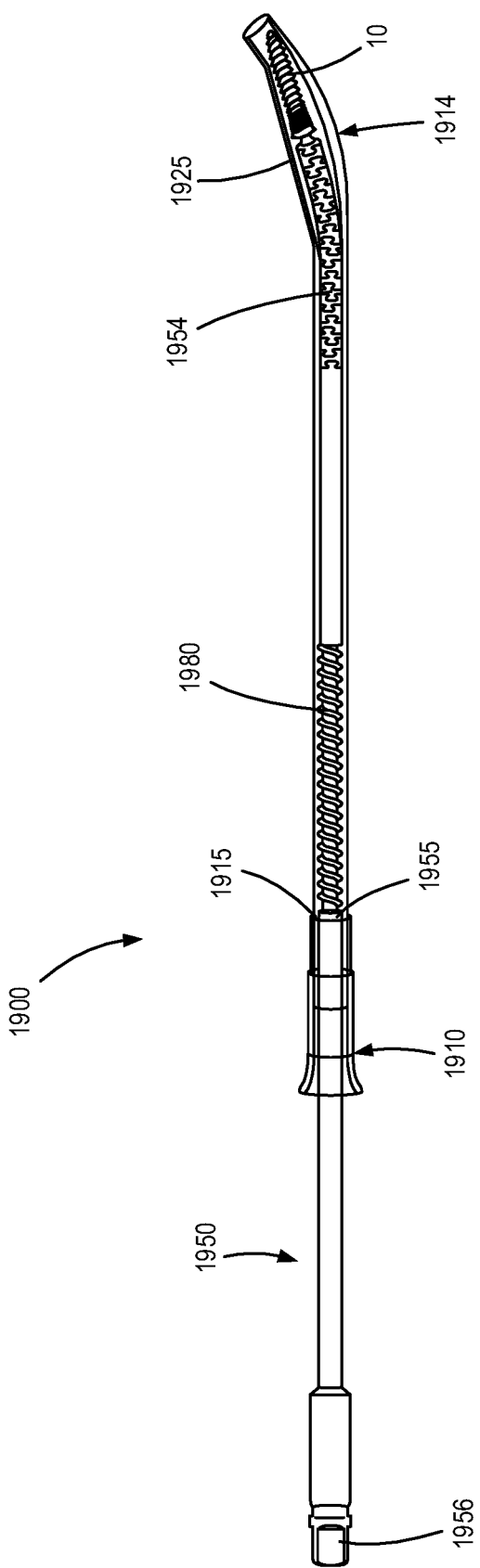
FIG. 20 is a phantom, perspective view of the instrument of FIG. 19, but illustrated in a retracted position with a bone screw retracted into the guide tube portion of the combined instrument.

In the retracted position illustrated in FIG. 20, bone screw 10 may be at least partially contained within angled portion 1914 of guide tube 1910. As previously discussed, guide tube 1910 may comprise a hood 1925 positioned along at least a portion of guide tube 1910. Hood 1925 may be used to cover an expanded region 1908 of a lumen of guide tube 1910, which may allow bone screw 10 to extend through the angled portion 1914 of guide tube 1910.

Figure 21:
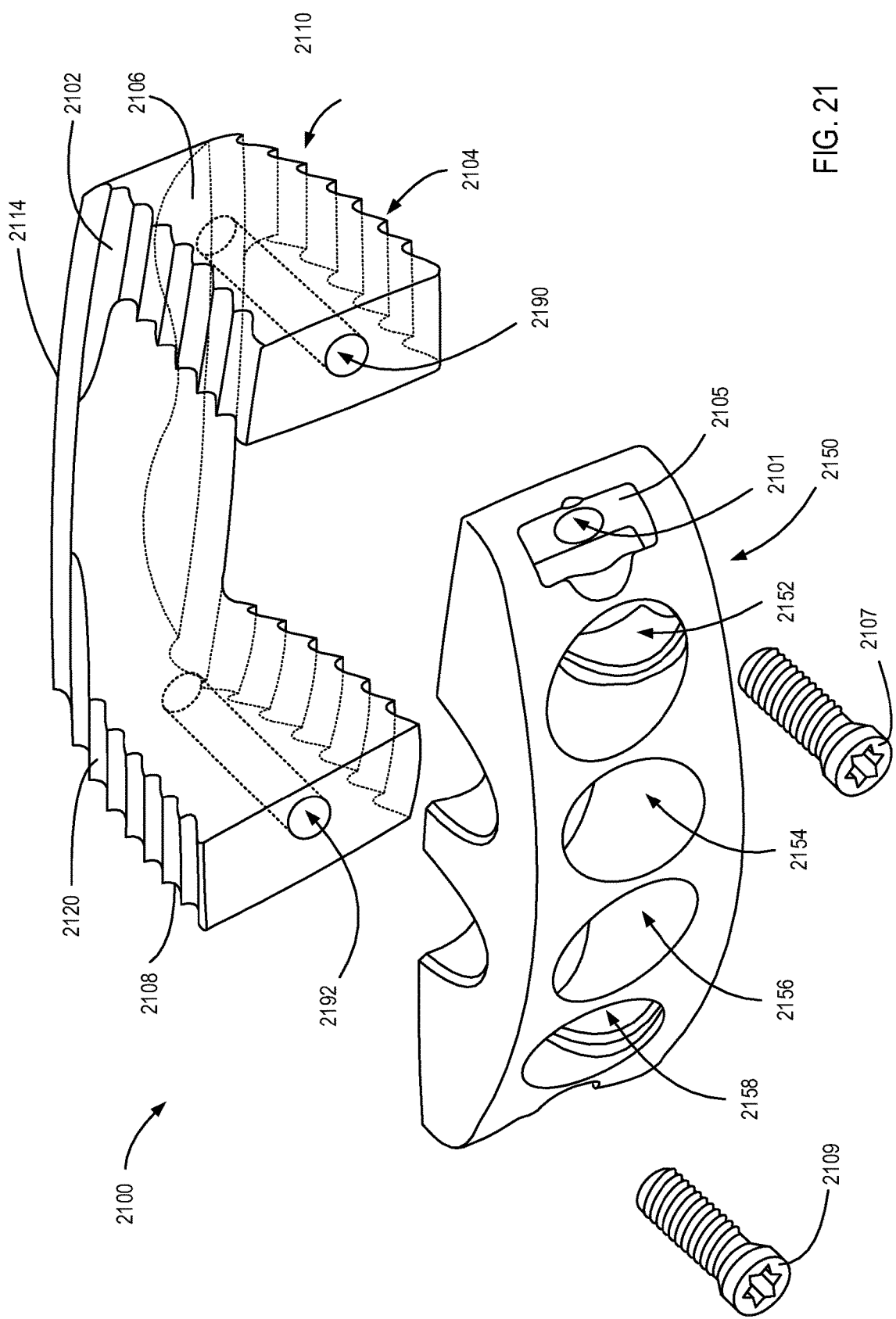
FIG. 21 is an exploded, perspective view of another embodiment of a stand-alone anterior lumbar interbody fusion spinal implant with a base portion of the implant shown in phantom.

FIG. 21 depicts yet another embodiment of a stand-alone ALIF implant 2100. Implant 2100 comprises a base portion 2110 and a secondary fastener portion 2150. In preferred embodiments, base portion 2110 and secondary portion 2150 comprise different materials such that implant 2100 may take advantage of the different characteristics of the two different materials in the same implant. For example, in some embodiments, base portion 2110 may comprise a silicon nitride ceramic material, another similar ceramic material, or another material that is not readily subject to receiving stable threads for use in fixation to vertebral bones without damaging the implant, and secondary fastener portion 2150 may comprise other materials more suitable for being threaded and/or engaging a threaded fastener, such as titanium metals, titanium alloys, or other metals.

Base portion 2110 of implant 2100 comprises an upper surface 2102, a lower surface 2104, a first sidewall 2106, a second sidewall 2108 opposite from sidewall 2106, and a rear end wall 2114. Unlike several embodiments previously discussed, implant 2100 lacks a front end wall. Instead, secondary portion 2150 bridges a gap between a first end of first sidewall 2106 and a corresponding first end of second sidewall 2108 so as to wholly define a second or front end wall of implant 2100 opposite from rear end wall 2114. In addition, base portion 2110 at least substantially comprises a "C" shape.

Upper and lower surfaces 2102 and 2104 may both comprise a plurality of engagement structures or teeth 2120. Teeth 2120 may be arranged in parallel rows that may each extend at least substantially perpendicular to the direction in which side walls 2106 and 2108 extend. Upper and lower surfaces 2102 and 2104 are also both defined in part by base portion 2110 and in part by secondary portion 2150.

Similarly, an opening is defined in part by base portion 2110 and in part by secondary portion 2150 when base portion 2110 has been coupled with secondary portion 2150. This opening may allow for ingrowth of bony material therethrough.

In the embodiment of FIG. 21, secondary portion 2150 is configured to be coupled with base portion 2110 by way of two locking members, namely locking member 2107 and locking member 2109. These locking members may comprise, for example, screws, bolts, pins, or the like. In the depicted embodiment, locking members 2107 and 2109 are threaded, and are received in corresponding threaded openings 2190 and 2192 formed within sidewalls 2106 and 2108, respectively.

In some embodiments, a recess 2105 may be formed within opposite ends of secondary portion 2150 such that no portion of the respective locking members 2107/2109 extends outside of a plane defined by a front surface of secondary portion 2150, as illustrated in FIG. 21. Openings 2101 may extend through such recesses 2105 (only one is visible in FIG. 21) on opposite ends of secondary fastener portion 2150 such that the head of locking members 2107 and 2109 sit within these recesses 2105 following assembly. Locking members 2107 and 2109 extend through openings 2101 and into respective openings 2190 and 2192 formed within opposing sidewalls of base portion 2110.

Secondary portion 2150 is further configured to receive fasteners, such as bone screws, therethrough. More particularly, secondary portion 2150 comprises four fastener openings, namely, fastener openings 2152, 2154, 2156, and 2158. Each of these fastener openings may be configured to receive a bone screw (not shown in the figure) or another such fastener therethrough. Fastener openings 2152, 2154, 2156, and 2158 may be threaded in some embodiments.

Figure 22A:
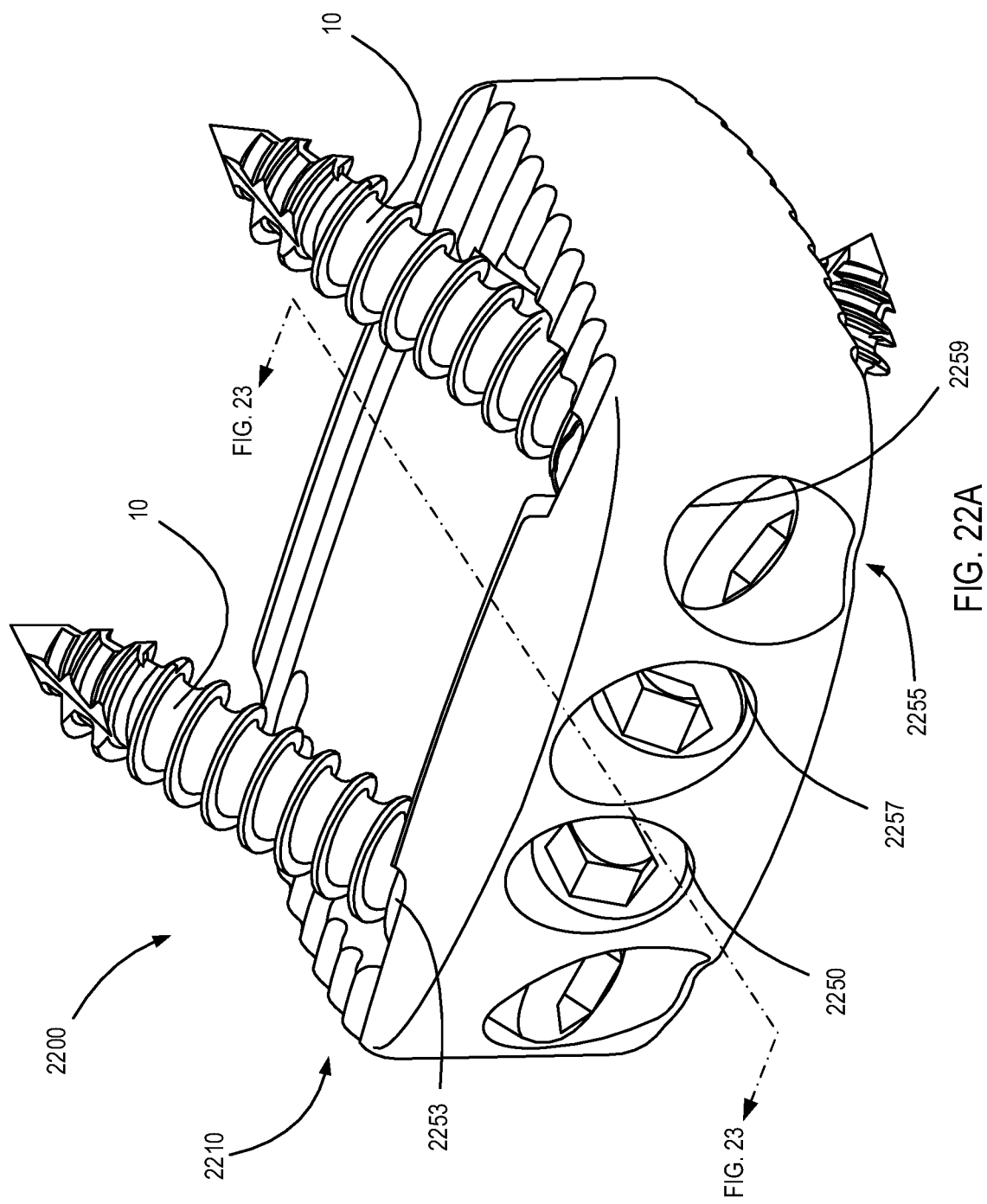
FIG. 22A is a perspective view of yet another embodiment of a stand-alone anterior lumbar interbody fusion spinal implant.
Figure 22B:
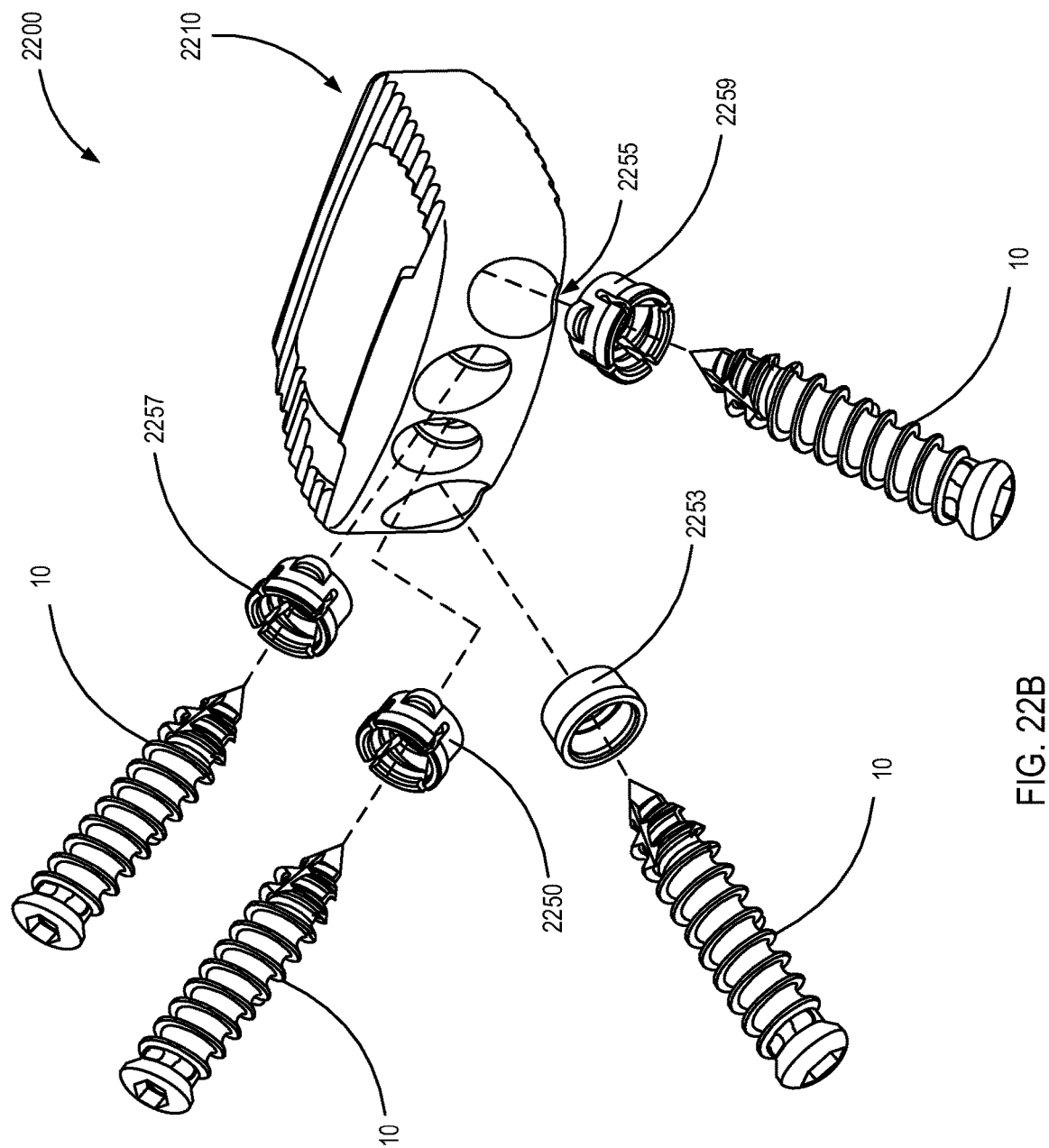
FIG. 22B is an exploded, perspective view of the implant of FIG. 22A.

FIGS. 22A and 22B depict another embodiment of a stand-alone ALIF implant 2200. Implant 2200 comprises a base portion 2210 and a plurality of secondary fastener portions, namely, secondary fastener portions 2250, 2253, 2257, and 2259. Each of these secondary fastener portions is configured to be received in a corresponding fastener opening formed within base portion 2210 and is configured to engage with a fastener, such as a bone screw, such that the respective secondary fastener portion is positioned in between the fastener/bone screw and the base portion 2210. In this manner, an implant, such as a stand-alone ALIF implant, another spinal implant, or another biomedical implant, may be primarily formed from a relatively non-threadable material, such as silicon nitride, and the secondary fastener portions 2250, 2253, 2257, and 2259, which may comprise a more-readily threadable material, such as titanium or another metal, may be threaded to serve as an interface between the bone screws 10 and the base portion 2210. In the depicted embodiment, secondary fastener portions 2250, 2253, 2257, and 2259 comprise sleeves having a cylindrical shape.

One or more of the various fastener openings may comprise a groove 2255 that may engage with a protrusion or another similar engagement structure formed on one or more of the secondary fastener portions 2250, 2253, 2257, and 2259 to prevent the secondary fastener portion(s) from rotating once installed. In some embodiments, groove 2255 may comprise an area of a fastener opening where the material defining the opening is naturally missing due to the exit angle of the fastener opening and the shape of the device in that region. Alternatively, a groove may be formed that would not otherwise be present in order to accommodate a protrusion or other similar engagement feature. An example of a protrusion on a secondary fastener portion for engaging groove 2255 can be seen in FIG. 24 at 2455 and is discussed in greater detail below. Of course, in alternative embodiments, a groove may instead be formed within a secondary fastener portion and may engage a corresponding protrusion formed within one or more of the fastener openings.

In preferred embodiments, base portion 2210 is made up of a first material and each of secondary fastener portions 2250, 2253, 2257, and 2259 is made up of a different material such that implant 2200 may take advantage of the different characteristics of the two different materials in the same implant. For example, in some preferred embodiments, base portion 2210 may comprise a silicon nitride ceramic material, another similar ceramic material, or another material that is not readily subject to receiving stable threads for use in fixation to vertebral bones without damaging the implant, and secondary fastener portions 2250, 2253, 2257, and 2259 comprise other materials more suitable for being threaded and/or engaging a threaded fastener, such as titanium metals, titanium alloys, or other metals.

Figure 23:
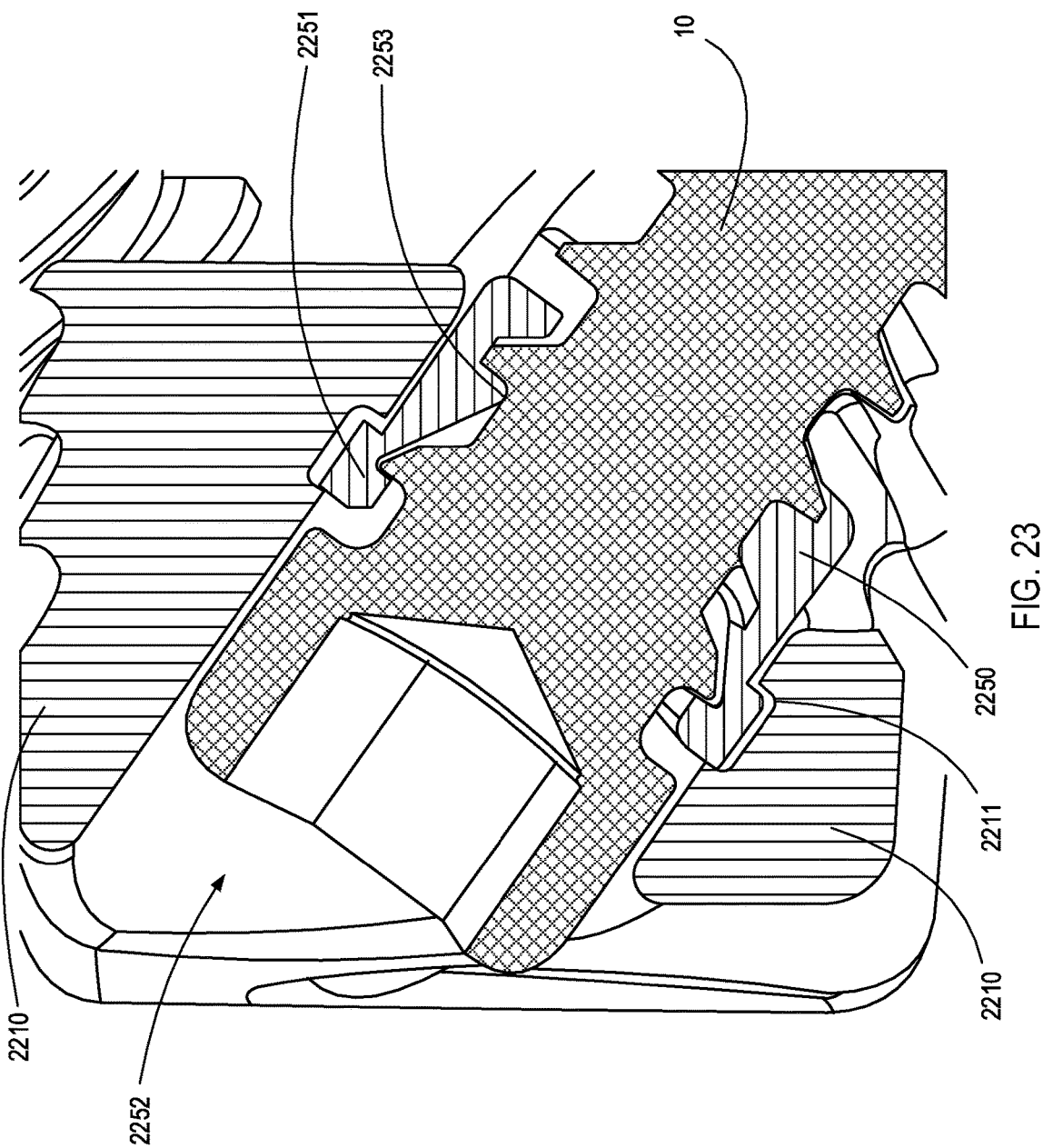
FIG. 23 is a cross-sectional view taken along line 23-23 in FIG. 22A.

As shown in the cross-sectional view of FIG. 23, secondary fastener portion 2250 may comprise an engagement feature 2251 configured to engage with a corresponding engagement feature 2211 of the base portion 2210. In the embodiment depicted in FIG. 23, the engagement feature 2251 of the secondary fastener portion 2250 comprises a protruding rim 2251, and the engagement feature 2211 of the base portion 2210 comprises a slot 2211 formed within a bone screw/fastener opening 2252. In some embodiments, slot 2211 may extend all of the way around a perimeter of opening 2252. Alternatively, slot 2211 may only be formed in one or more discrete locations within the perimeter of opening 2252. In such embodiments, rotation of the secondary fastener portion may be restricted by the interface between the rim/engagement feature of the secondary fastener portion and the slot/engagement feature of the base portion.

Secondary fastener portion 2250 further comprises an internal thread 2253. In certain preferred embodiments, internal thread 2253 may extend about an internal periphery of the secondary fastener portion 2250 between about one turn and about two turns.

Figure 24:
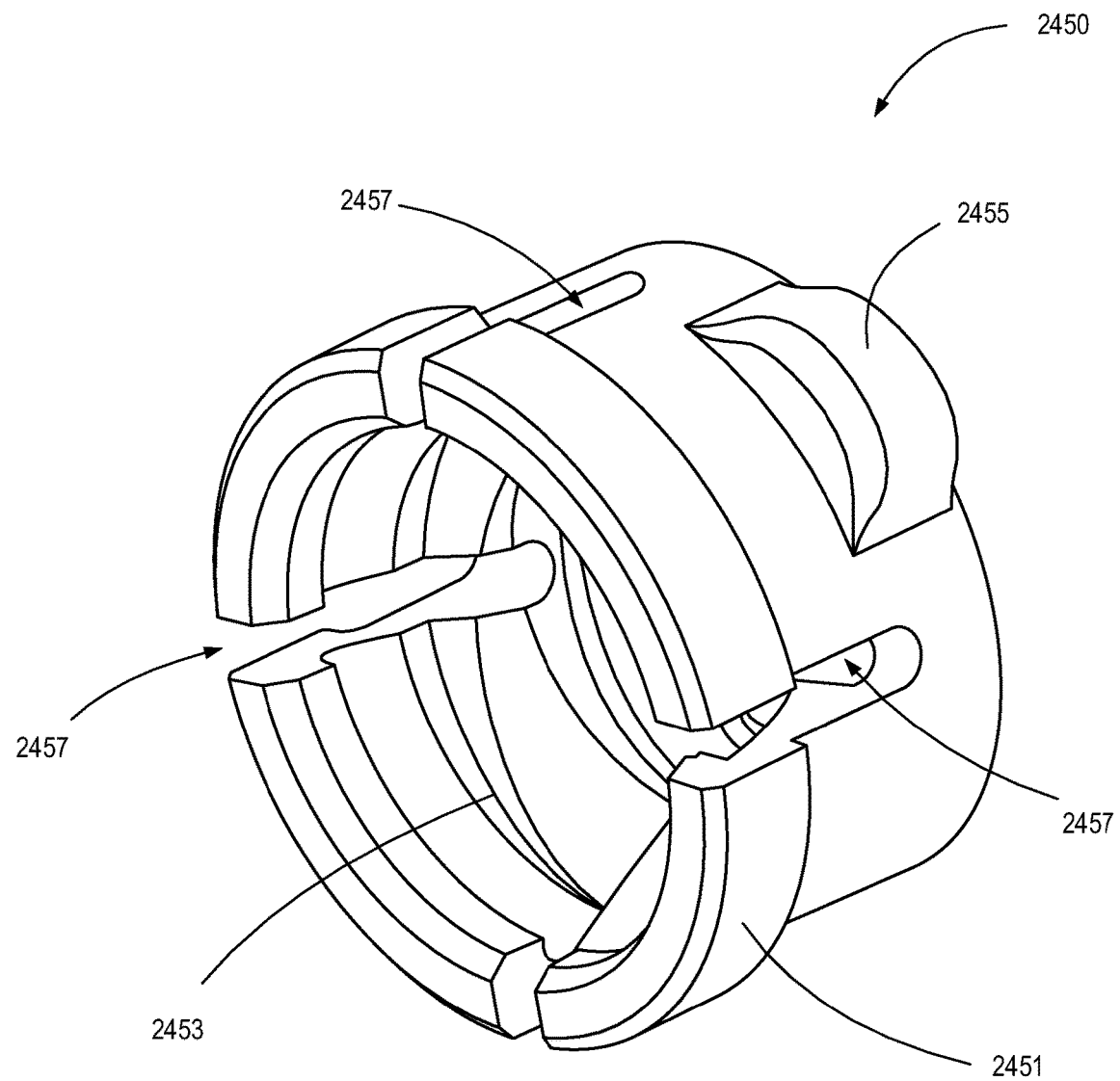
FIG. 24 is a perspective view of an embodiment of a secondary fastener member comprising a sleeve.
Figure 25:
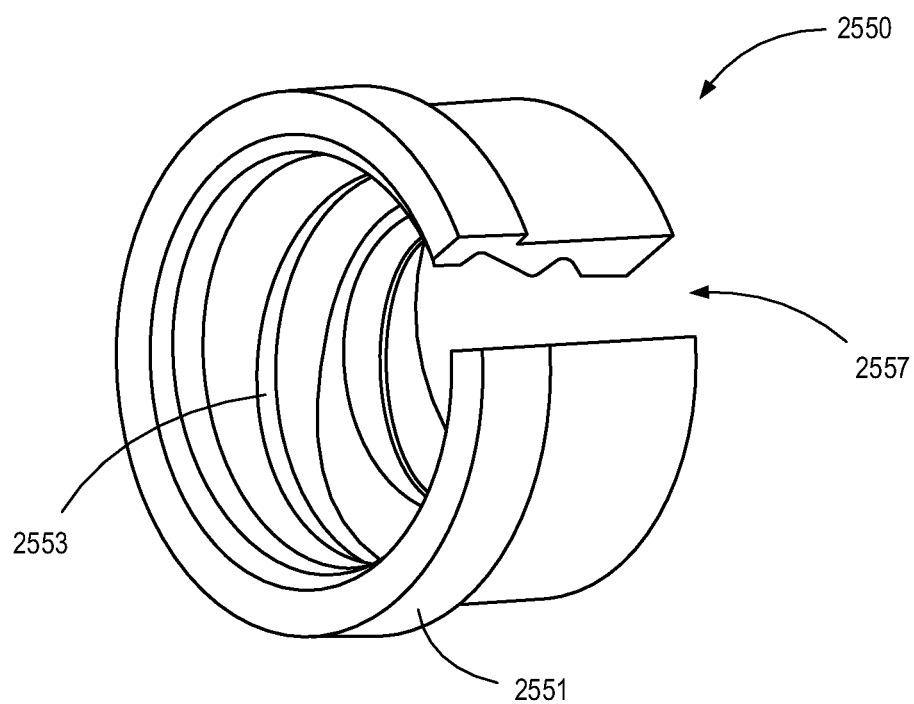
FIG. 25 is a perspective view of an alternative embodiment of a secondary fastener member comprising a sleeve.
Figure 26:
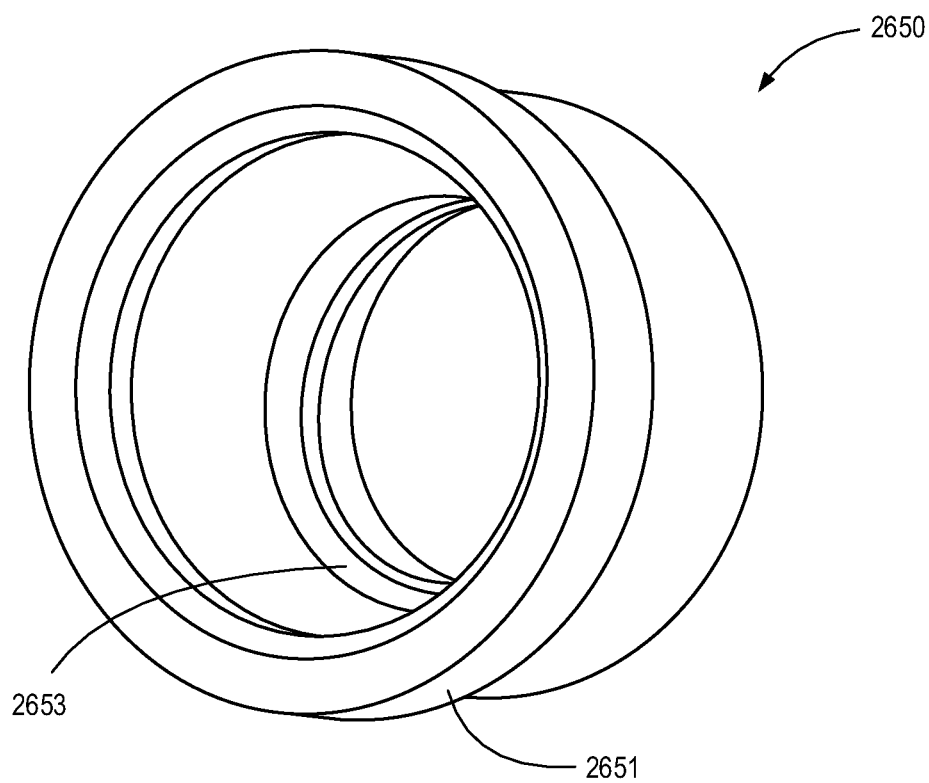
FIG. 26 is a perspective view of still alternative embodiment of a secondary fastener member comprising a sleeve.

FIGS. 24-26 depict alternative embodiments of secondary fastener portions comprising sleeves that may be used as individual interfaces between a fastener opening of a portion, such as a base portion, of an implant and a bone screw or other fastener. FIG. 24 depicts a first such sleeve 2450. Sleeve 2450 comprises an internal thread 2453, as previously described. Sleeve 2450 further comprises a protruding rim 2451, as also previously described. Rim 2451 may allow sleeve 2450 to be fixedly engaged within a corresponding slot or similar engagement feature of a portion of an implant.

Sleeve 2450 also comprises a plurality of partial slits 2457 formed at regular intervals about sleeve 2450. Partial slits 2457 may allow sleeve 2450 to flex in desirable manners during installation of sleeve 2450 in a particular fastener opening of an intervertebral or other implant. In particular, slits 2457 may be flexed inwardly to allow rim 2451 to decrease in diameter and thereby allow rim 2451 to be seated within a slot or another engagement feature of an implant.

Sleeve 2450 further comprises a protrusion 2455 that extends radially from an exterior surface of sleeve 2450. Protrusion 2455 may be configured to be received in a groove formed within a fastener opening of an implant, or a part of an implant. For example, protrusion 2455 may be configured to fit within groove 2255 of implant 2200. Protrusion 2455 and groove 2255 are examples of means for preventing a sleeve or another secondary fastener portion from rotating with respect to a base portion or another portion of an implant. Another such example is one or more slots, such as slot 2211, that are formed in one or more discrete locations within the perimeter of a fastener opening, along with a corresponding protrusion or protrusions formed on a sleeve or another secondary fastener portion.

FIG. 25 depicts another alternative embodiment of a secondary fastener member comprising a sleeve 2550. Sleeve 2550 comprises an internal thread 2553 and a protruding rim 2551, as previously described. Sleeve 2550 further comprises a single full slit 2557 that extends all the way along the length of sleeve 2550 in one location such that sleeve 2550 comprises a split-ring sleeve. As with partial slits 2457 in sleeve 2450, slit 2557 may allow sleeve 2550 to flex inwardly to allow rim 2551 to decrease in diameter and thereby allow rim 2551 to be seated within a slot or another engagement feature of an implant.

FIG. 26 depicts yet another alternative embodiment of a secondary fastener member comprising a sleeve 2650. Sleeve 2650 comprises an internal thread 2653 and a protruding rim 2651, as previously described. However, sleeve 2650 lacks the slits previously described.

Figure 27:
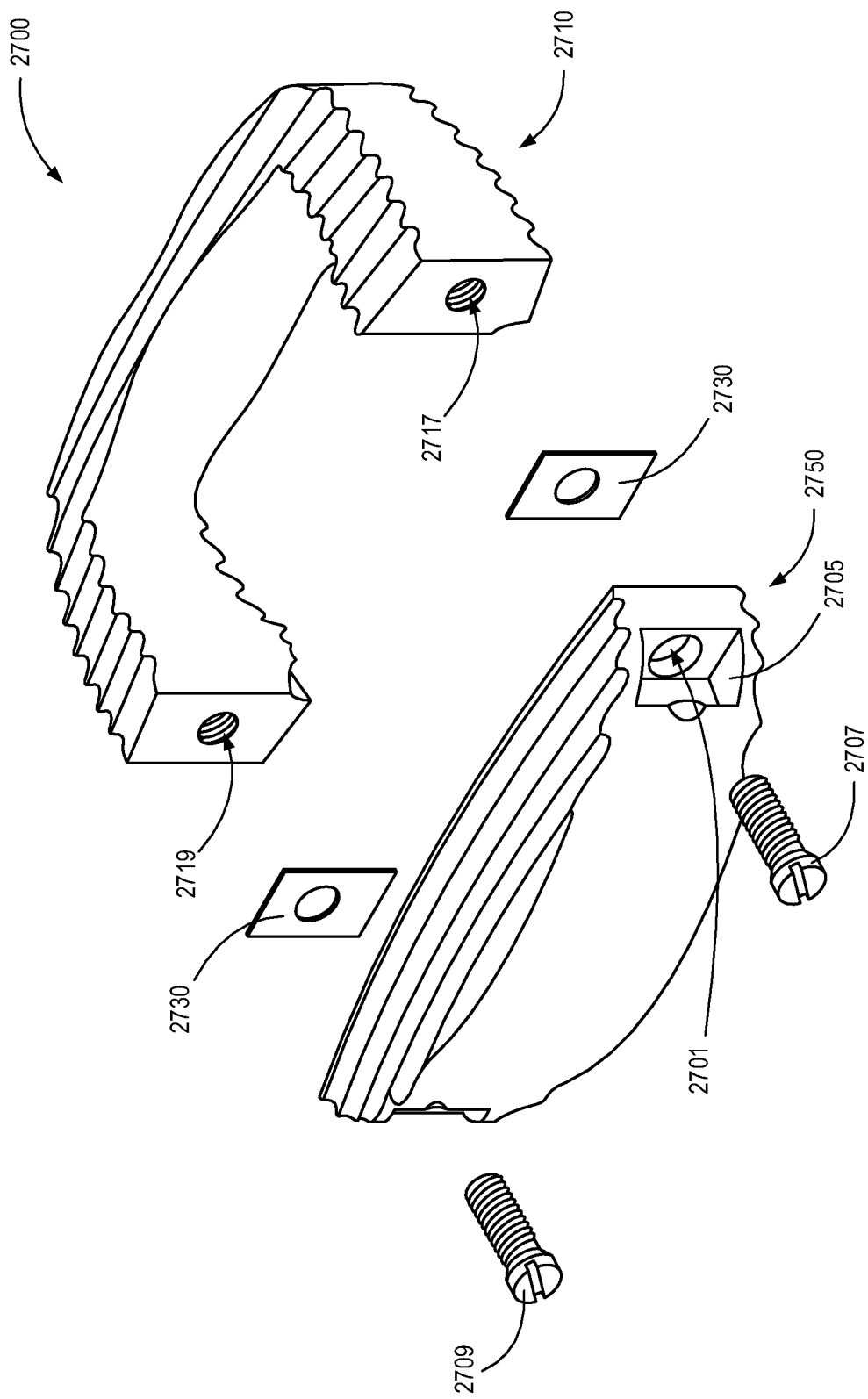
FIG. 27 is an exploded, perspective view of another embodiment of a stand-alone anterior lumbar interbody fusion spinal implant.

FIG. 27 depicts another alternative a stand-alone ALIF implant 2700. Implant 2700 comprises a base portion 2710 and a secondary fastener portion 2750. In preferred embodiments, base portion 2710 and secondary portion 2750 comprise different materials such that implant 2700 may take advantage of the different characteristics of the two different materials in the same implant, as previously described.

Implant 2700 is similar to implant 2100 in most respects. However, unlike implant 2100, implant 2700 comprises teeth on both base portion 2710 and secondary portion 2750. Moreover, washers 2730 may be provided in between base portion 2710 and secondary portion 2750. In some embodiments, washers 2730 may comprise an intermediate material, such as PEEK (polyetheretherketone), or another material that may comprise a more desirable interface between the material of base portion 2710 (which, in some embodiments, comprises a relatively non-threadable material) and the material of secondary portion 2750 (which, in some embodiments, comprises a relatively more threadable material).

As with implant 2100, implant 2700 is configured such that secondary portion 2750 may be coupled with base portion 2710 by way of two locking members, namely locking member 2707 and locking member 2709. These locking members may comprise, for example, screws, bolts, pins, or the like. In the depicted embodiment, locking members 2707 and 2709 are threaded, and are received in corresponding threaded openings 2717 and 2719, respectively, formed within opposing sidewalls of base portion 2710.

Another pair of openings 2701 (only one of which is visible in FIG. 27) may be formed within a corresponding pair of recesses 2705 formed within opposite ends of secondary portion 2750. Locking members 2707/2709 extend through openings 2701 and openings 2717/2719 to couple secondary portion 2750 with base portion 2710.

Although secondary portion 2750 is not shown as having bone screw/fastener openings formed therein (i.e., similar to fastener openings 2152, 2154, 2156, and 2158), it should be understood that one or more such openings may be formed therein if desired.

Figure 28:
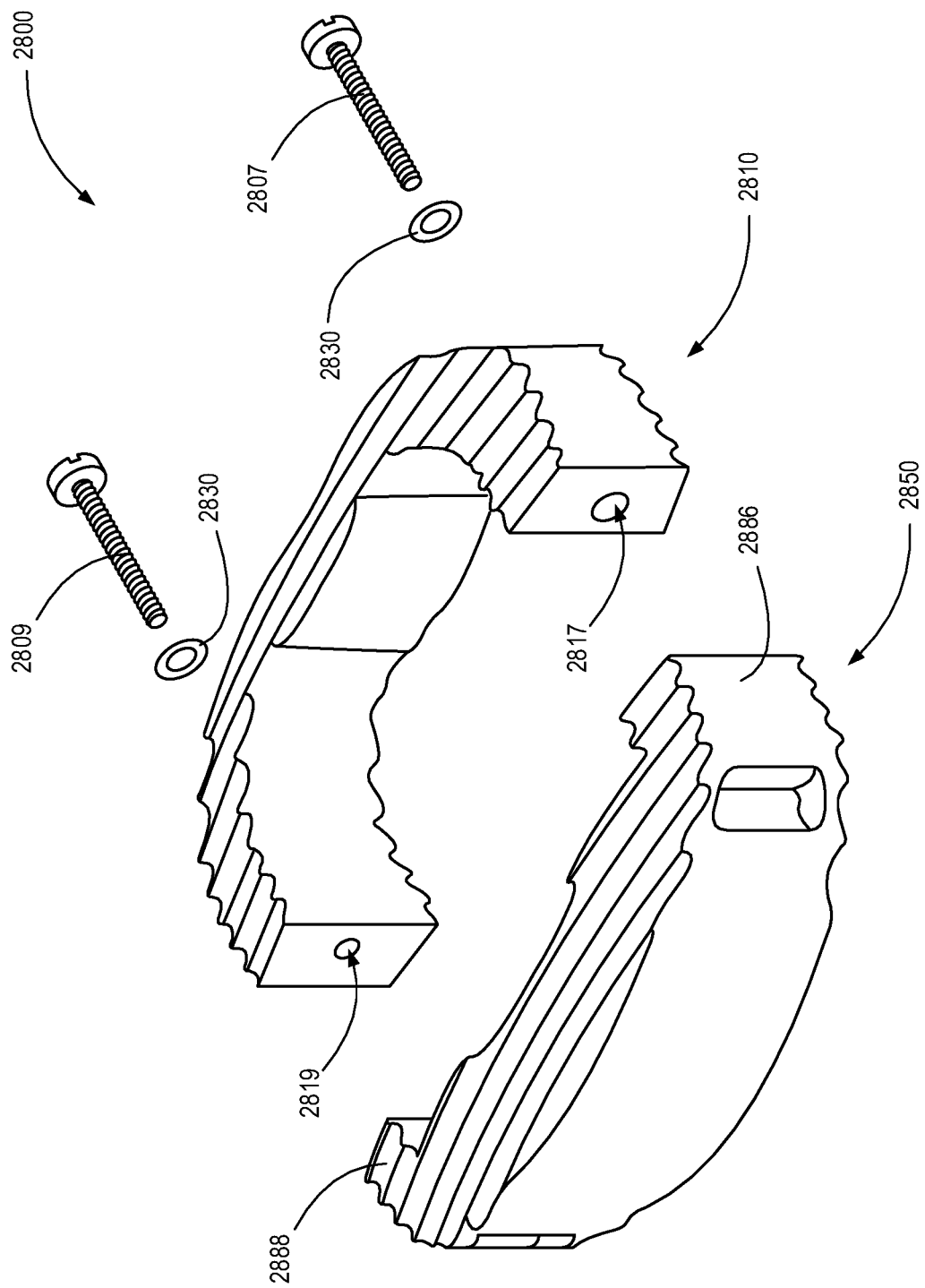
FIG. 28 is an exploded, perspective view of still another embodiment of a stand-alone anterior lumbar interbody fusion spinal implant.

FIG. 28 depicts another embodiment of a stand-alone ALIF implant 2800 comprising a base portion 2810 and a secondary portion 2850. Implant 2800 further comprises locking member openings 2817 and 2819 formed within and extending along the entire length of opposing sidewalls of base portion 2810. Similar openings (not visible in FIG. 28) may be formed within opposing flanges 2886 and 2888 of secondary portion 2850 such that two locking members 2807 and 2809 may be used to fixedly couple base portion 2810 with secondary portion 2850. In some embodiments, washers 2830 may be used, either in between locking members 2807/2809 and base portion 2810, or between base portion 2810 and secondary fastener portion 2850. In addition, as previously mentioned in connection with implant 2700, although secondary portion 2850 is not shown as having bone screw/fastener openings formed therein (i.e., similar to fastener openings 2152, 2154, 2156, and 2158), it should be understood that one or more such openings may be formed therein if desired.

Figure 29:
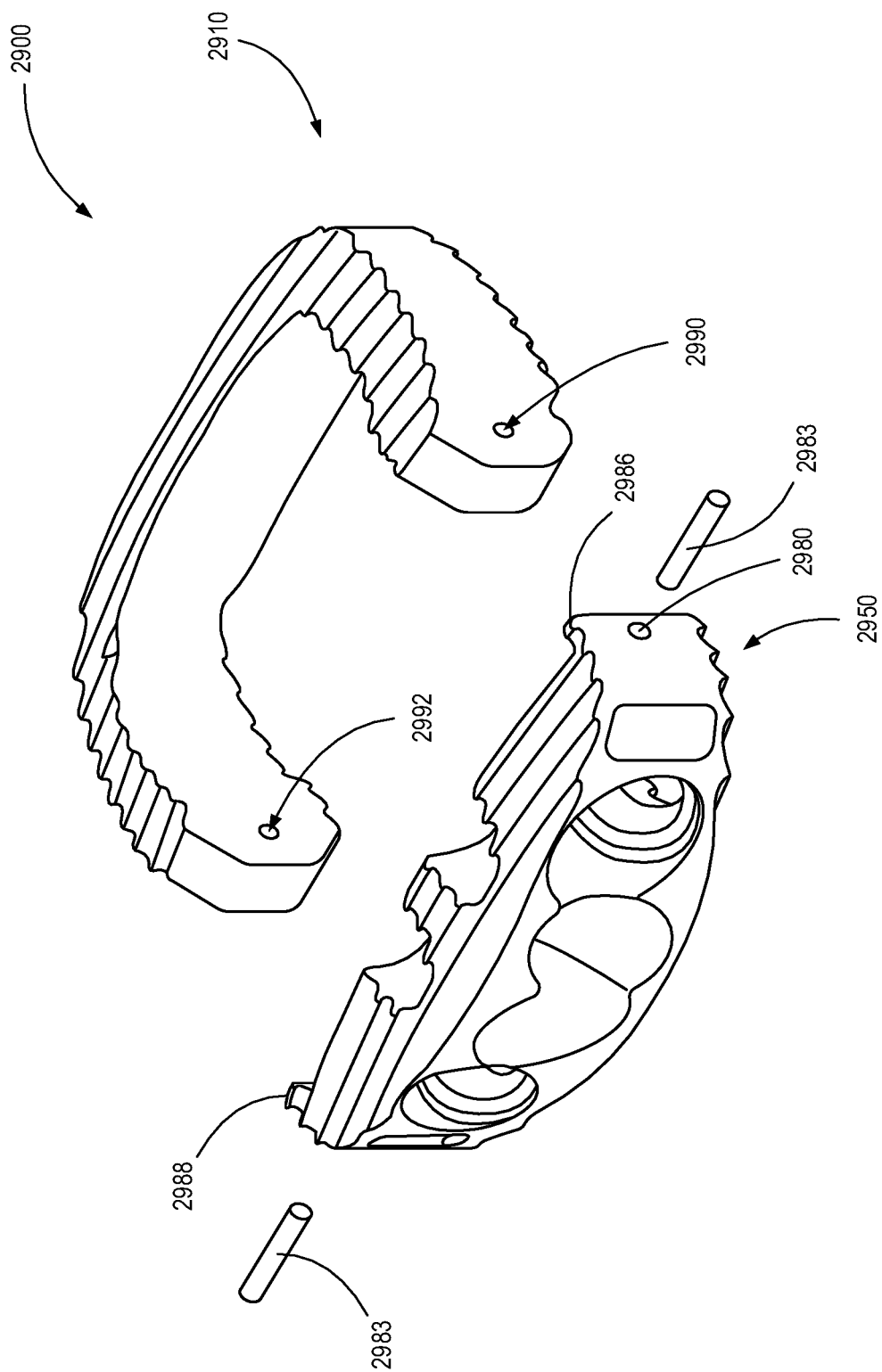
FIG. 29 is an exploded, perspective view of yet another embodiment of a stand-alone anterior lumbar interbody fusion spinal implant.

FIG. 29 depicts still yet another embodiment of a stand-alone ALIF implant 2900 comprising a base portion 2910 and a secondary fastener portion 2950. Implant 2900 is similar to implant 1000 in that it comprises locking member openings 2990 and 2992 formed adjacent to a distal end of opposing sidewalls of base portion 2910. However, these locking member openings 2990 and 2992, both of which are configured to receive a pin 2983 or another locking member, extend horizontally rather than vertically.

In addition, rather than comprising recesses formed by opposing portions of secondary fastener portion 2950, secondary fastener portion 2950 comprises two opposing flanges 2986 and 2988 that are configured to extend around opposing exterior surfaces of a portion of base portion 2910 defining openings 2990 and 2992. In this manner, secondary fastener portion 2950 may be coupled with base portion 2910 by extending opposing flanges 2986 and 2988 around the opposing tips of base portion 2910 such that openings 2990/2992 are aligned with openings 2980 and its corresponding opening on the opposite side (not visible in FIG. 29), and inserting pins 2983 or other locking members through the aligned openings on both sides of implant 2900. Pins 2983 may be secured within these openings by a friction fit or may be threaded.

It will be understood by those having skill in the art that changes may be made to the details of the above-described embodiments without departing from the underlying principles presented herein. Any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein. The scope of the present invention should, therefore, be determined only by the following claims.

The invention claimed is:
1. An intervertebral spinal implant, comprising:
a base portion; and
a secondary portion comprising at least one opening configured to receive at least one fastener for engaging a vertebral body of a patient's spine,
wherein:
the secondary portion wholly defines a front end wall surface of the intervertebral spinal implant;
the base portion and the secondary portion collectively define at least one of an upper surface and a lower surface of the intervertebral spinal implant;
the at least one opening comprises a plurality of protrusions positioned along a surface of the at least one opening that engage with respective recessions positioned about a proximal portion of the at least one fastener; and
the plurality of protrusions are defined by two opposing ramped surfaces that lead to a central portion of each protrusion of the plurality of protrusions.
2. The intervertebral spinal implant of claim 1, wherein the central portion comprises an at least substantially flat surface.
3. The intervertebral spinal implant of claim 1, wherein the two opposing ramped surfaces each comprise a flat surface positioned at an angle with respect to the central portion.

4. The intervertebral spinal implant of claim 1, wherein the two opposing ramped surfaces each comprise a concave surface.

5. The intervertebral spinal implant of claim 1, wherein the plurality of protrusions are arranged in a helical pattern about the surface of the at least one opening.

6. The intervertebral spinal implant of claim 5, wherein the helical pattern substantially matches a corresponding helical pattern of threads of the at least one fastener.

7. The intervertebral spinal implant of claim 5, wherein the plurality of protrusions are tapered such that the height of each of the plurality of protrusions increases from a proximal portion of the at least one opening to a distal portion of the at least one opening.

8. The intervertebral spinal implant of claim 1, wherein the respective recessions are arranged in a helical pattern or a circular pattern.

9. The intervertebral spinal implant of claim 1, wherein the at least one fastener is a bone screw.

10. The intervertebral spinal implant of claim 9, wherein the respective recessions are positioned in a threaded section of the proximal portion of the bone screw.

11. The intervertebral spinal implant of claim 9, wherein the respective recessions are positioned in an unthreaded section of the proximal portion of the bone screw.

12. The intervertebral spinal implant of claim 1, wherein the base portion comprises a first material and the secondary portion comprises a second material that is distinct from the first material.

13. An intervertebral spinal implant, comprising:
a base portion comprising a plurality of openings; and
a plurality of secondary fastener portions comprising at least one protrusion on an outer surface configured to be received in a groove formed within the plurality of openings in the base portion and a plurality of protrusions positioned along an inner surface configured to engage with respective recessions positioned about a proximal portion of a respective fastener,
wherein:
each of the plurality of secondary fastener portions is configured to be received in one of the plurality of openings in the base portion,
each of the secondary fastener portions is configured to engage with the respective fastener such that the respective secondary fastener portion is positioned in between the respective fastener and the base portion; and
the plurality of protrusions are defined by two opposing ramped surfaces and a central portion formed between the opposing ramped surfaces; and
each of the plurality of secondary fastener portions comprises an internal thread which extends about an internal periphery of each respective one of the plurality of secondary fastener portions between about one turn and about two turns.

14. The intervertebral spinal implant of claim 13, wherein the base portion comprises a first material and the plurality of secondary fastener portions comprise a second material distinct from the first material.

15. The intervertebral spinal implant of claim 13, wherein the respective fastener is a bone screw and the respective recessions are positioned in an unthreaded section of the proximal portion of the bone screw.

16. An intervertebral spinal implant, comprising:
a base portion comprising a plurality of openings; and
a plurality of secondary fastener portions comprising at least one protrusion on an outer surface configured to be received in a groove formed within the plurality of openings in the base portion and a plurality of protrusions positioned along an inner surface configured to engage with respective recessions positioned about a proximal portion of a respective fastener,
wherein:
each of the plurality of secondary fastener portions is configured to be received in one of the plurality of openings in the base portion,
each of the secondary fastener portions is configured to engage with the respective fastener such that the respective secondary fastener portion is positioned in between the respective fastener and the base portion; and
the plurality of protrusions are defined by two opposing ramped surfaces and a central portion formed between the opposing ramped surfaces;
wherein the plurality of protrusions is arranged in a helical pattern about the inner surface of each of the plurality of the secondary fastener portions that substantially matches a corresponding helical pattern of threads of the respective fastener.

17. The intervertebral spinal implant of claim 16, wherein the base portion comprises a first material and the plurality of secondary fastener portions comprise a second material distinct from the first material.

18. The intervertebral spinal implant of claim 16, wherein the respective fastener is a bone screw and the respective recessions are positioned in an unthreaded section of the proximal portion of the bone screw.

* * * * *